United States Patent
Boden et al.

(10) Patent No.: US 9,630,991 B2
(45) Date of Patent: Apr. 25, 2017

(54) βSHEET TAPES RIBBONS IN TISSUE ENGINEERING

(71) Applicant: University of Leeds, Leeds (GB)

(72) Inventors: Neville Boden, Leeds (GB); Amalia Aggeli, Thessaloniki (GR); Eileen Ingham, Leeds (GB); Jennifer Kirkham, Leeds (GB)

(73) Assignee: University of Leeds, Leeds (GB)

( * ) Notice: Subject to any disclaimer, the term of this patent is extended or adjusted under 35 U.S.C. 154(b) by 0 days.

(21) Appl. No.: 14/887,592

(22) Filed: Oct. 20, 2015

(65) Prior Publication Data

US 2016/0046670 A1   Feb. 18, 2016

Related U.S. Application Data

(60) Division of application No. 14/062,768, filed on Oct. 24, 2013, now Pat. No. 9,193,764, which is a division of application No. 12/729,046, filed on Mar. 22, 2010, now Pat. No. 8,586,539, which is a continuation-in-part of application No. 10/521,628, filed as application No. PCT/GB03/03016 on Jul. 15, 2003, now Pat. No. 7,700,721.

(30) Foreign Application Priority Data

Jul. 15, 2002 (GB) .................................. 0216286.5

(51) Int. Cl.
| | |
|---|---|
| A61K 6/02 | (2006.01) |
| A61K 8/64 | (2006.01) |
| A61L 27/22 | (2006.01) |
| A61L 27/38 | (2006.01) |
| A61L 27/56 | (2006.01) |
| A61Q 19/00 | (2006.01) |
| A61Q 5/00 | (2006.01) |
| C07K 14/00 | (2006.01) |
| C07K 7/06 | (2006.01) |
| A61L 27/52 | (2006.01) |
| A61Q 11/00 | (2006.01) |

(52) U.S. Cl.
CPC ................ C07K 7/06 (2013.01); A61K 8/64 (2013.01); A61L 27/22 (2013.01); A61L 27/227 (2013.01); A61L 27/38 (2013.01); A61L 27/52 (2013.01); A61L 27/56 (2013.01); A61Q 5/00 (2013.01); A61Q 11/00 (2013.01); A61Q 19/00 (2013.01)

(58) Field of Classification Search
CPC ......... A61K 6/02; A61K 8/64; A61L 2430/02; A61L 27/22; A61L 27/227; A61L 27/38; A61L 27/56; A61Q 19/00; A61Q 5/00; C07K 14/001; C07K 7/06
USPC ................... 514/18.6, 1.1; 530/325; 435/395
See application file for complete search history.

(56) References Cited

U.S. PATENT DOCUMENTS

| | | | |
|---|---|---|---|
| 6,034,211 A | 3/2000 | Kelly | |
| 7,101,990 B2 | 9/2006 | Contreras et al. | |
| 7,678,883 B2 | 3/2010 | Cheng et al. | |
| 7,700,721 B2 | 4/2010 | Boden et al. | |
| 8,586,539 B2 | 11/2013 | Boden et al. | |
| 9,062,312 B2 | 6/2015 | Rouviere et al. | |
| 9,101,687 B2 | 8/2015 | Boden et al. | |
| 9,187,527 B2 | 11/2015 | Boden et al. | |
| 9,193,764 B2 | 11/2015 | Boden et al. | |
| 2003/0162696 A1 | 8/2003 | Mihara | |
| 2006/0154852 A1 | 7/2006 | Boden et al. | |
| 2010/0040879 A1 | 2/2010 | Koopmans et al. | |
| 2010/0040880 A1 | 2/2010 | Koopmans et al. | |
| 2010/0234304 A1 | 9/2010 | Boden et al. | |
| 2013/0012457 A1 | 1/2013 | Boden et al. | |
| 2014/0044649 A1 | 2/2014 | Boden et al. | |
| 2014/0186313 A1 | 7/2014 | Boden et al. | |
| 2015/0299266 A1 | 10/2015 | Boden et al. | |
| 2016/0058871 A1 | 3/2016 | Ingham et al. | |

FOREIGN PATENT DOCUMENTS

WO   WO 03/006494 A1   1/2003

OTHER PUBLICATIONS biowww.net/buffer-reagent/1x-Phosphate-Buffered-Saline.html (printed Mar. 22, 2010).
Aggeli et al., "pH as a Trigger of Peptide β-Sheet Self-Assembly and Reversible Switching between Nematic and Isotropic Phases," *J. Am. Chem. Soc.* 125:9619-9628 (2003).
Aggeli et al., "Responsive Gels Formed by the Spontaneous Self-Assembly of Peptides Into Polymeric β-Sheet Tapes," *Nature* 386:259-262 (1997).
Aggeli et al., "Self-Assembling Homopolymeric Peptide Tapes in Aqueous Solution," Peptide Science—Present and Future (eds.), pp. 30-33 (1999).
Aggeli et al., "Structure and Dynamic of Self-Assembling β-Sheet Peptide Tapes by Dynamic Light Scattering," *Biomacromolecules* 2:378-388 (2001).
Bell et al., "Self-assembling peptides as injectable lubricants for osteoarthritis," *Journal of Biomedical Materials Research*, Part A, pp. 235-246 (2006).
Carrick et al., "Effect of ionic strength on the self-assembly, morphology and gelation of pH responsive beta-sheet tape-forming peptides," *Tetrahedron*, 63: 7457-7467 (2007).
Credentist Ag, "Regenerating Teeth" from Credentis Innovation Brochure, credentis.com, printed on/or after 2012, Accessed Jun. 1, 2015.
Fishwick et al., "Structures of Helical β-Tapes and Twisted Ribbons: The Role of Side-Chain Interactions on Twist and Bend Behavior," *Nano Lett.* 3:1475-1479 (2003).
Fukushima, "Self-Induced Helix-Sheet Conformational Transitions of an Amphiphilic Peptide," *Polym. J.* 27:819-830 (1995).
Kyle et al., "Recombinant Self-Assembling Peptide as Biomaterials for Tissue Engineering," *Biomaterials* 31:9395-9405, 2010.

(Continued)

Primary Examiner — Julie Ha
(74) Attorney, Agent, or Firm — Klarquist Sparkman, LLP

(57) ABSTRACT

There is described a material comprising tapes, ribbons, fibrils or fibers characterized in that each of the ribbons, fibrils or fibers have an antiparallel arrangement of peptides in a β-sheet tape-like substructure.

35 Claims, 10 Drawing Sheets

(56) References Cited

OTHER PUBLICATIONS

Nyrkova et al., "Fibril Stability in Solutions of Twisted β-Sheet Peptides: A New Kind of Micellization in Chiral Systems," *Eur. Phys. J.* 17:481-497 (2000).

Nyrkova et al., "Self-Assembly and Structure Transformations in Living Polymers Forming Fibrils," *Eur. Phys. J.* 17:499-513 (2000).

Protopapa et al., "Interaction of self-assembling beta-sheet peptides with phospholipid monolayers: The effect of serine, threonine, glutamine and asparagine amino acid side chains," *Electrochimica Acta*, 55(9): 3368-3375 (2010).

Zelezetsky and Tossi, "Alpha-Helical Antimicrobial Peptides—Using a Sequence Template to Guide Structure-Activity Relationship Studies," *Biochim Biophys. Acta* 1758:1436-1449, 2006.

Liquid Crystalline Peptide Solutions and Gel Scaffolds

Nematic fluid solution of oriented peptide fibrils

Nematic gel scaffold: the fibre-like junctions are made of entwined fibrils

βSHEET TAPES RIBBONS IN TISSUE ENGINEERING

CROSS REFERENCE TO RELATED APPLICATIONS

This is a divisional application of U.S. application Ser. No. 14/062,768 filed on Oct. 24, 2013, which is a divisional of Ser. No. 12/729,046 filed Mar. 22, 2010, now U.S. Pat. No. 8,586,539, which is a continuation-in-part application of U.S. application Ser. No. 10/521,628 filed Sep. 8, 2005, now U.S. Pat. No. 7,700,721 (both herein incorporated by reference), which is the U.S. National Stage of International Application No. PCT/GB2003/003016, filed Jul. 15, 2003 (published in English under PCT Article 21(2)), which in turn claims the benefit of Great Britain patent application no. 0216286.5 filed Jul. 15, 2002.

FIELD

This disclosure relates to novel supramolecular aggregates, polymers and networks made by beta-sheet self-assembly of rationally-designed peptides, and their uses as for example as responsive industrial fluids (oil exploration), as personal care products, as tissue reconstruction devices (e.g., dental reconstructive devices), or as controlled drug delivery systems.

BACKGROUND

International Patent Application No WO 96/31528 (Boden et al.) describes novel rationally designed peptides which self-assemble in one dimension to form beta sheet tape-like polymers. The tapes above a critical peptide concentration (typically above 0.3% v/v peptide) become physically entangled and gel their solutions in organic solvents or in water (FIG. 1). The peptide gels possess the specific property of being programmable to switch from the gel state to a fluid or stiffer gel state in response to external chemical or physical triggers.

It has recently been found that the tapes having chemically distinct opposing surfaces can give rise to an hierarchy of other self-assembled, supramolecular structures as a function of increasing peptide concentration: ribbons (two stacked tapes), fibrils (many ribbons stacked together) and fibres (entwined fibrils) [1-3] (FIG. 2). All these beta-sheet polymers appear twisted because of the peptide chirality. A theoretical model has been developed which rationalises this self-assembly process of beta-sheet forming peptides using a set of energetic parameters $\epsilon_j$ (FIG. 1). The magnitudes of $\epsilon_j$ define the peptide concentration ranges over which each type of polymer will be stable.

SUMMARY

We have shown that by appropriate peptide design we can produce tapes, ribbons, fibrils or fibres controllable by changes of the pH, the ionic strength of the solution or temperature. In particular, peptides can be designed which self-assemble to form one or other of these polymers at a certain concentration and in a specific pH range, but which are transformed into another polymer structure or dissociate into the monomeric random coil state in a different pH range, according to the specific amino acid sequence of the peptide.

We have recently discovered that this hierarchy of polymers can be formed not only by a single type of peptide (homopeptide polymers), but also by mixing complementary peptides together (alternating co-polymers). For example, we have shown that peptide $P_{11}$-8 (Tablex 1A and 1C) adopts monomeric random coil conformation and forms fluid isotropic solutions at pH<7 in water. This behaviour stems from the three ornithine groups on the peptide. At pH lower than their effective pKa, the ornothine side-chains are ionised, and the intermolecular electrostatic repulsions generated by these positively charged groups prevent beta-sheet self-assembly.

Thus, provided herein is a material comprising ribbons, fibrils or fibres characterised in that each of the ribbons, fibrils or fibres have an antiparallel arrangement of peptides in a β-sheet tape-like substructure.

When the material substantially comprises fibrils, the fibrils may be comprised in a network of fibrils interconnected at fibre-like junctions.

Also provided is a material wherein the material comprises a self assembling peptide (SAP) wherein the SAP forms a tape in an aqueous medium and is made up of 3 or more polar/neutral amino acids and a plurality of charged amino acids.

The polar/neutral amino acids, which may be the same or different, and can be selected from the group including glutamine, serine, asparagine, orthinine, cysteine, lysine, histidine, glutamic acid and threonine.

We further provide a material wherein the amino acids are positively charged and form a gel at a pH of higher than or equal to a neutral pH. Alternatively, we provide a material wherein the amino acids are negatively charged and form a gel at a pH of lower than or equal to a neutral pH.

An exemplary material in this aspect of the disclosure is SAP $P_{11}$-8 (SEQ ID NO: 2).

We further provide a material wherein the amino acid chain is extended to include a bioactive peptide sequence, or wherein the amino acid chain is attached to a therapeutically active molecule.

The material may comprise a SAP which forms ribbons and/or fibrils in an aqueous solution and wherein the SAP has a primary structure in which at least 50% of the amino acids comprise an alternating structure of polar and apolar amino acids.

The polar amino acids include from 1 to 3 charged amino acids per 11 amino acids. Preferably, the SAP is selected from the group $P_{11}$-9 (SEQ ID NO: 3), $P_{11}$-12 (SEQ ID NO: 4), $P_{11}$-15 (SEQ ID NO: 7), $P_{11}$-16 (SEQ ID NO: 8), $P_{11}$-17 (SEQ ID NO: 9), $P_{11}$-18 (SEQ ID NO: 10), $P_{11}$-19 (SEQ ID NO: 11) and $P_{11}$-20 (SEQ ID NO: 12).

Exemplary peptides of the present disclosure are recited in Tables 1A, 1B, 1C and 1D.

TABLE 1A

Primary structures of rationally designed peptides.

| Peptide Name | Primary Structure* | SEQ ID NO: |
|---|---|---|
| $P_{11}$-4 | $CH_3CO$-Q-Q-R-F-E-W-E-F-E-Q-Q-$NH_2$ | 1 |
| $P_{11}$-8 | $CH_3CO$-Q-Q-R-F-O-W-O-F-E-Q-Q-$NH_2$ | 2 |
| $P_{11}$-9 | $CH_3CO$-S-S-R-F-E-W-E-F-E-S-S-$NH_2$ | 3 |
| $P_{11}$-12 | $CH_3CO$-S-S-R-F-O-W-O-F-E-S-S-$NH_2$ | 4 |
| $P_{11}$-13 | $CH_3CO$-E-Q-E-F-E-W-E-F-E-Q-E-$HN_2$ | 5 |

TABLE 1A-continued

Primary structures of rationally designed peptides.

| Peptide Name | Primary Structure* | SEQ ID NO: |
|---|---|---|
| $P_{11}$-14 | $CH_3CO$-Q-Q-O-F-O-W-O-F-O-Q-Q-$NH_2$ | 6 |
| $P_{11}$-15 | $CH_3CO$-N-N-R-F-E-W-E-F-E-N-N-$NH_2$ | 7 |
| $P_{11}$-16 | $CH_3CO$-N-N-R-F-O-W-O-F-E-N-N-$NH_2$ | 8 |
| $P_{11}$-17 | $CH_3CO$-T-T-R-F-E-W-E-F-E-T-T-$NH_2$ | 9 |
| $P_{11}$-18 | $CH_3CO$-T-T-R-F-O-W-O-F-E-T-T-$NH_2$ | 10 |
| $P_{11}$-19 | $CH_3CO$-Q-Q-R-Q-O-Q-O-Q-E-Q-Q-$NH_2$ | 11 |
| $P_{11}$-20 | $CH_3CO$-Q-Q-R-Q-E-Q-E-Q-E-Q-Q-$NH_2$ | 12 |

*The N- and C- termini of the peptides are always blocked with $CH_3CO$- and $NH_2$- respectively. O symbolizes ornithine amino acid side chains.

TABLE 1B

Amphiphilic self assembling peptides carrying a net negative 2 charge in physiological solution.

| Peptide Name | Net Charge at pH 7.5 | Polar Amino Acid | Peptide Structure (SEQ ID NO:) |
|---|---|---|---|
| $P_{11}$-9 | −2 | Serine | 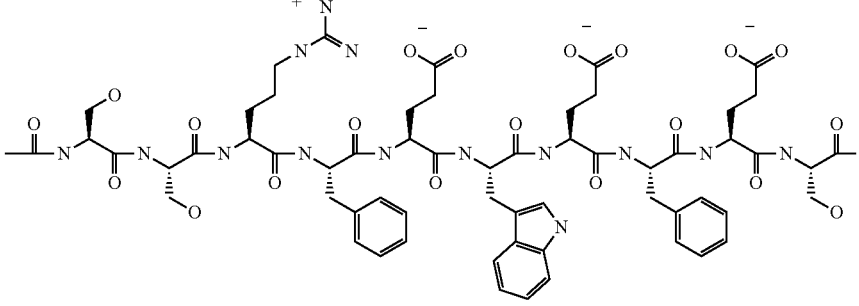 <br> S  S  R  F  E  W  E  F  E  S  S <br> (3) |
| $P_{11}$-15 | −2 | Asparagine | 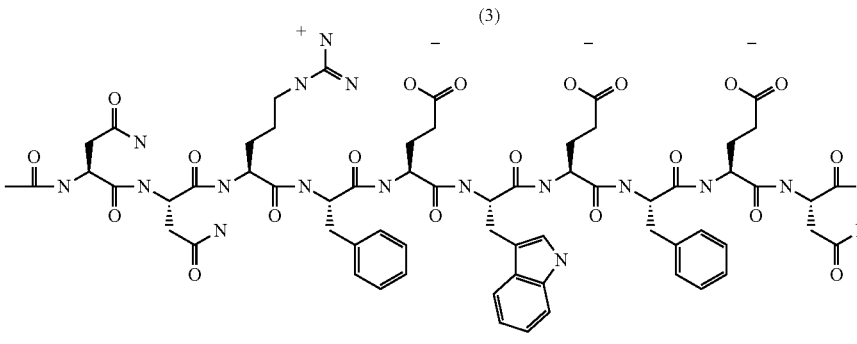 <br> N  N  R  F  E  W  E  F  E  N  N <br> (7) |
| $P_{11}$-17 | −2 | Threonine | 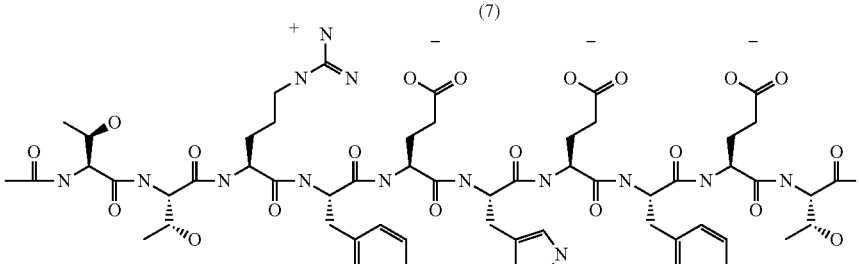 <br> T  T  R  F  E  W  E  F  E  T  T <br> (9) |

TABLE 1C

Amphiphilic self assembling peptides carrying a net positive 2 charge in physiological solution.

| Peptide Name | Net Charge at pH 7.5 | Polar Amino Acid | Peptide Structure (SEQ ID NO:) |
|---|---|---|---|
| $P_{11}$-8 | +2 | Glutamine | Q Q R F O W O F E Q Q (2) |
| $P_{11}$-12 | +2 | Serine | S S R F O W O F E S S (4) |
| $P_{11}$-16 | +2 | Asparagine | N N R F O W O F E N N (8) |

TABLE 1C-continued

Amphiphilic self assembling peptides carrying a net positive 2 charge in physiological solution.

| Peptide Name | Net Charge at pH 7.5 | Polar Amino Acid | Peptide Structure (SEQ ID NO:) |
|---|---|---|---|
| $P_{11}$-18 | +2 | Threonine | |

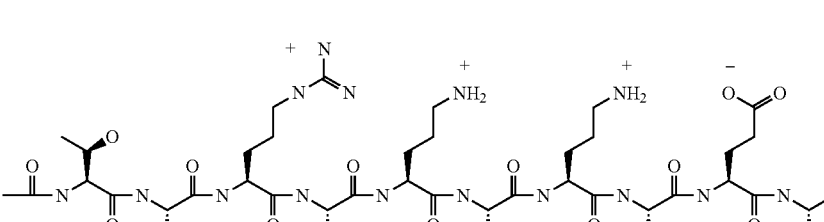

T T R F O W O F E T T (10)

TABLE 1D

Polar self assembling peptides carrying a net negative 2 charge in physiological solution.

| Peptide Name | Net Charge at pH 7.5 | Polar Amino Acid | Peptide Structure (SEQ ID NO:) |
|---|---|---|---|
| $P_{11}$-19 | +2 | Glutamine | |

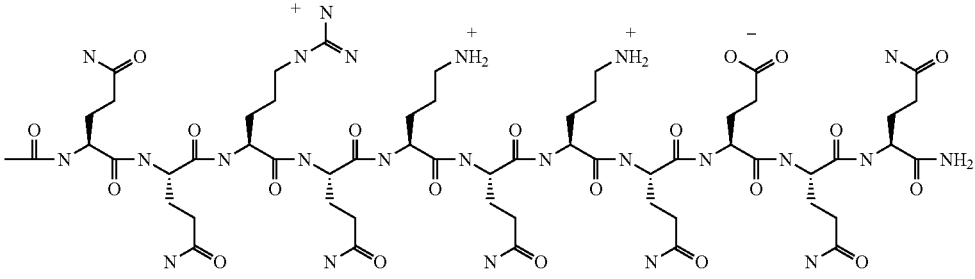

Q Q R Q O Q O Q E Q Q (11)

| $P_{11}$-20 | −2 | Glutamine | |

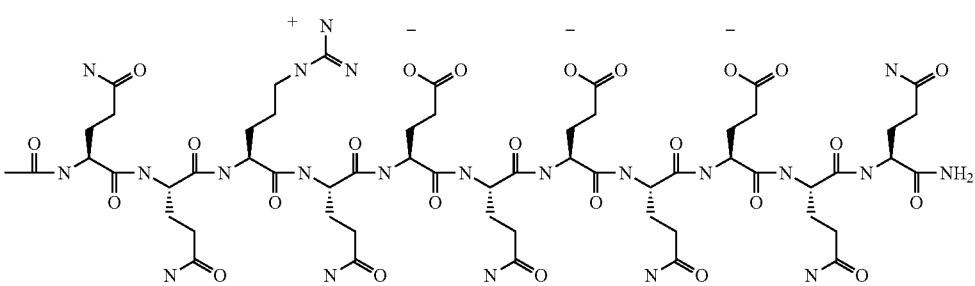

Q Q R Q E Q E Q E Q Q (12)

The peptides provided herein are preferably 11 residues in length and have a conserved arginine residue at position 3.

Preferably, the amino acid residues at positions 1 and 2 are the same and are selected from the group comprising serine (SS), glutamine (QQ), threonine (TT) and asparagines (NN), Preferably, the amino acid residues at positions 10 and 11 are the same and are selected from the group comprising serine (SS), glutamine (QQ), threonine (TT) and asparagines (NN), Preferably, the amino acid residues at positions 1 and 2 and 10 and 11 are the same so that they are all either serine (SS), glutamine (QQ), threonine (TT) or asparagines (NN).

Preferably, the amino acid residue at position 4 is either phenylalanine or glutamine.

Preferably, the amino acid residues at positions 4 and 5 are selected from the pairs of the group comprising phenylalanine and glutamic acid, phenylalanine and ornithine, glutamine and glutamic acid and glutamine and ornithine.

The material may be suitable for use in, inter alia, tissue engineering, cell culture medium, and/or dental treatment.

We also provide a material wherein the material comprises a self assembling peptide (SAP) wherein the SAP forms a tape in an aqueous medium and is made up of 3 or more polar/neutral amino acids and a plurality of charged amino acids.

In some examples, the SAP is isolated. An "isolated" biological component (such as a protein) has been substantially separated or purified away from other biological components present in the cell of an organism, or the organism itself, in which the component may naturally occur, such as other chromosomal and extra-chromosomal DNA and RNA, proteins and cells. In addition, proteins that have been "isolated" include proteins purified by standard purification methods. The term also embraces proteins prepared by recombinant expression in a host cell as well as chemically synthesized proteins. For example, an isolated SAP is one that is substantially separated from other peptides.

The polar/neutral amino acids, which may be the same or different, may be selected from the group including glutamine, serine, asparagine, orthinine, cysteine, lysine, histidine, glutamic acid and threonine.

In one example, the peptides have a polar amino acid selected from the group consisting of serine, asparagines, threonine and glutamine.

The apolar amino acids, which may be the same or different, are selected from the group including phenylalanine, tryptophan, valine, leucine, isoleucine and methionine.

We further provide a material wherein the amino acid chain is extended to include a bioactive peptide sequence, or wherein the amino acid chain is attached to a therapeutically active molecule.

In one example, in this aspect of the disclosure the SAP is $P_{11}$-8 (SEQ ID NO: 2).

We also provide a material wherein the SAP is soluble in a highly ionic medium. In this aspect of the disclosure, the SAP may comprise a ratio of net charged amino acids to total amino acids of from 1:11 to 4:11.

The material may be suitable for use in, inter alia, tissue engineering, cell culture medium, and/or dental treatment.

We further provide a material wherein the complementary peptide tapes are made up of 3 or more polar amino acids of which some are charged amino acids wherein the ratio of charged amino acids to total amino acids is 3:11 or greater.

We further provide a material wherein the amino acid chain is extended to include a bioactive peptide sequence, or wherein the amino acid chain is attached to a therapeutically active molecule.

The material may be suitable for use in, inter alia, tissue engineering, cell culture medium, and/or dental treatment.

Thus, according to a further feature of the disclosure we provide alternate co-polymer beta-sheet polymeric tapes, ribbons, fibrils and fibres made by the self-assembly of more than one complementary peptides. The complementarity of the peptide may be originating from their charges e.g., net positive charge on one peptide and net negative charge on the other peptide.

Also provided is a composition that includes ribbons, fibrils or fibres and a physiological concentration of salt (such as 120 to 160 mM NaCl, for example 140 to 150 mM NaCl or 145 to 150 mM NaCl, for example about 145 mM NaCl), wherein the composition is at a physiological pH (such as pH 7 to 8, for example pH 7.2 to 7.6, or pH 7.4 or pH 7.5), and wherein the peptide is present at a concentration of at least 15 mg/ml in the composition (for example 15 mg/ml to 100 mg/ml, 15 mg/ml to 60 mg/ml, 15 mg/ml to 50 mg/ml, 15 mg/ml to 35 mg/ml, 20 mg/ml to 50 mg/ml or 20 mg/ml to 35 mg/ml). Each of the ribbons, fibrils or fibres has an antiparallel arrangement of peptides in a β-sheet tape-like substructure at physiological pH and physiological salt concentrations, wherein each peptide or pair of complementary peptides comprises a net −2 or a +2 charge, and wherein the peptide is selected from the group comprising $P_{11}$-8, $P_{11}$-9, $P_{11}$-12, $P_{11}$-15, $P_{11}$-16, $P_{11}$-17, $P_{11}$-18 and $P_{11}$-20 as set forth in Table 1A.

The foregoing and other features of the disclosure will become more apparent from the following description of the figures.

SEQUENCE LISTING

Figure 1:
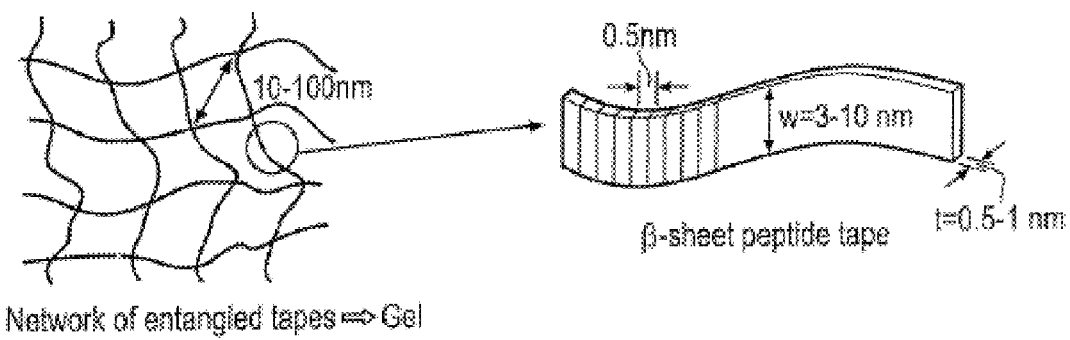
FIG. 1: Schematic representation of peptides in beta-strand conformation (represented as vertical lines) hydrogen bonding in one dimension with each other to form long self-assembling beta-sheet tapes. The width of the tape is determined by the length of the peptide molecules. The thickness of the tape is equal to the thickness of a beta-strand. The surface properties of the tapes are defined by the end groups of the peptide amino acid side-chains. The tapes are also shown to entangle to form a gel network in a good solvent.
Figure 2:
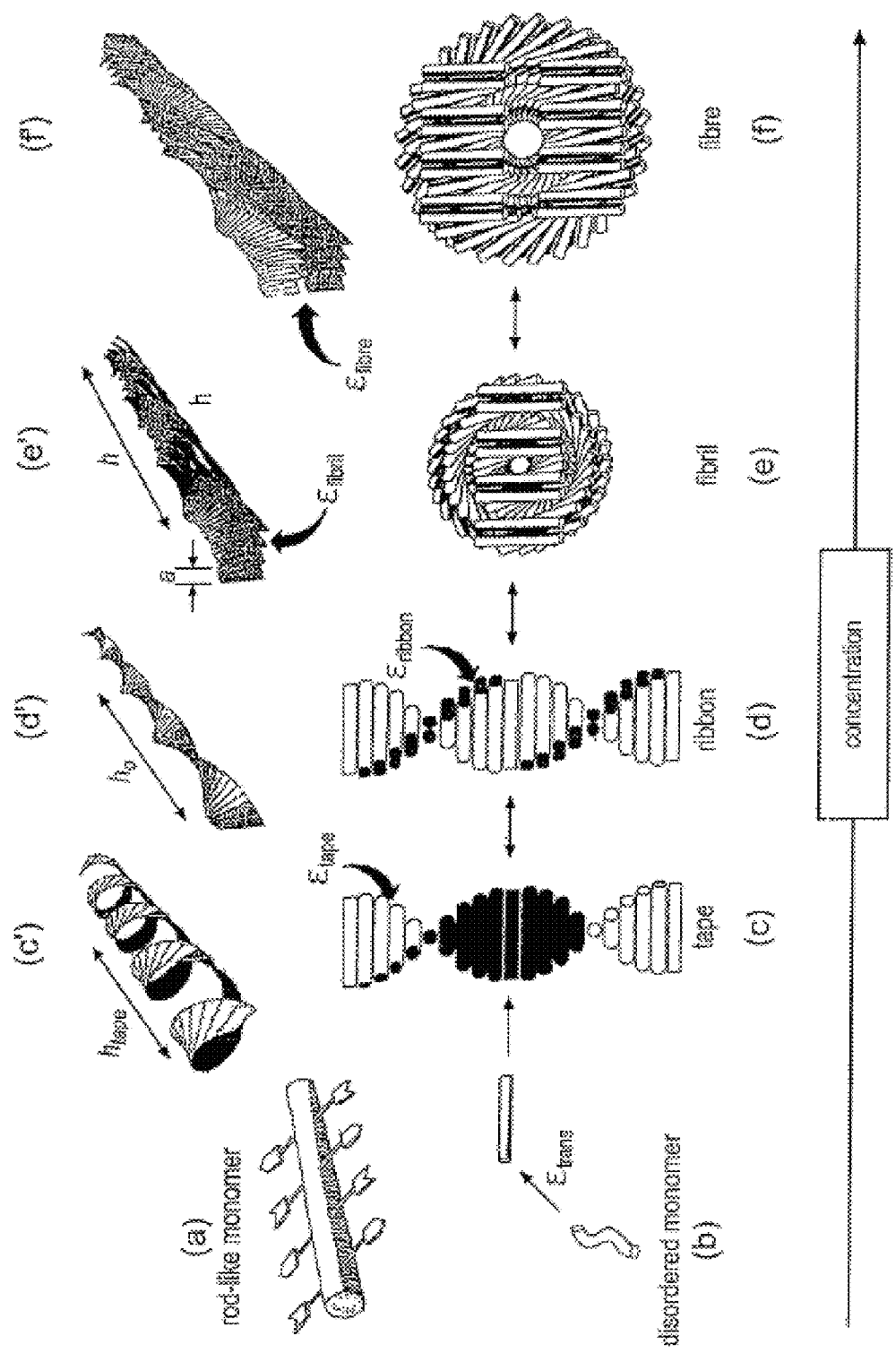
FIG. 2. Model of hierarchical self-assembly of beta-sheet forming peptides. Each peptide in beta-strand conformation, is depicted as a chiral rod-like unit (a). Local arrangements (c-f) and the corresponding global equilibrium conformations (c'-f') for the hierarchical self-assembling structures formed in solutions of chiral molecules (a), which have complementary donor and acceptor groups, shown by arrows, via which they interact and align to form tapes (c). The black and the white surfaces of the rod (a) are reflected in the sides of the helical tape (c) which is chosen to curl towards the black side (c'). The outer sides of the twisted ribbon (d), of the fibril (e) and of the fibre (f) are all white. One of the fibrils in the fibre (f') is drawn with darker shade for clarity. (e) & (f) show the front views of the edges of fibrils and fibres, respectively. Geometrical sizes (the numbers in parentheses show the values of the corresponding geometric sizes for $P_{11}$-I and $P_{11}$-II peptides, based on X-ray diffraction data and molecular modelling): inter-rod separation in a beta-sheet tape $b_2$ ($b_2$=0.47 nm); tape width, equal to the length of a rod, $b_1$ ($b_1$=4 nm); inter-ribbon distance in the fibril, $\alpha$ ($\alpha$=1.6-2 nm for $P_{11}$-I, and $\alpha$=2-2.4 nm for $P_{11}$-II).
Figure 3:
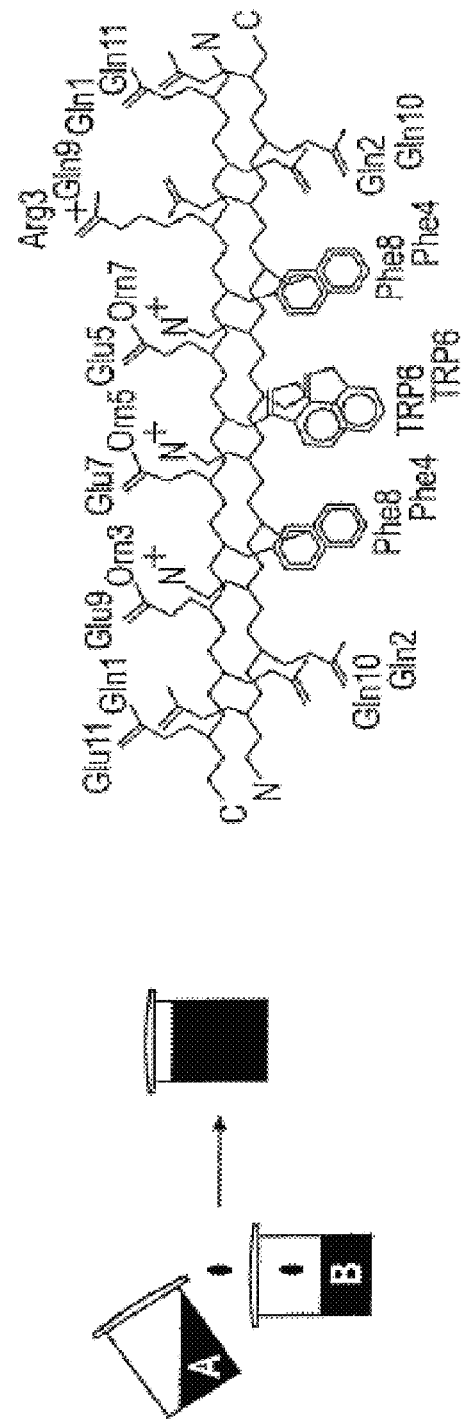
FIG. 3: Alternating copeptide polymeric gels.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~8 kb), which was created on Oct. 20, 2015, which is incorporated by reference herein. In the accompanying sequence listing:

SEQ ID NO: 1 is the amino acid sequence for P11-4.
SEQ ID NO: 2 is the amino acid sequence for P11-8.
SEQ ID NO: 3 is the amino acid sequence for P11-9.
SEQ ID NO: 4 is the amino acid sequence for P11-12.
SEQ ID NO: 5 is the amino acid sequence for P11-13.
SEQ ID NO: 6 is the amino acid sequence for P11-14.
SEQ ID NO: 7 is the amino acid sequence for P11-15.
SEQ ID NO: 8 is the amino acid sequence for P11-16.
SEQ ID NO: 9 is the amino acid sequence for P11-17.
SEQ ID NO: 10 is the amino acid sequence for P11-18.
SEQ ID NO: 11 is the amino acid sequence for P11-19.
SEQ ID NO: 12 is the amino acid sequence for P11-20.
SEQ ID NO: 13 is the amino acid sequence for P11-2.
SEQ ID NO: 14 is the amino acid sequence for P11-21.
SEQ ID NO: 15 is the amino acid sequence for P11-22.
SEQ ID NO: 16 is the amino acid sequence for P11-23.
SEQ ID NO: 17 is the amino acid sequence for P11-3.
SEQ ID NO: 18 is the amino acid sequence for P11-5.

DETAILED DESCRIPTION

The singular forms "a," "an," and "the" refer to one or more than one, unless the context clearly dictates otherwise. For example, the term "comprising a peptide" includes single or plural peptide and is considered equivalent to the phrase "comprising at least one peptide." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

The tapes, ribbons, fibrils and fibres are increasingly more rigid structures [1]. For example we have found that the persistence length l of single tapes formed by an 11-residue peptide $P_{11}$-1 in water is ca 0.3 µm, whilst the persistence lengths of ribbons and fibrils formed by a variant $P_{11}$-2 peptide in water are 1 and 20-70 µm respectively (Table 1).

We have also shown that above a certain peptide concentration $c_{I/N}$ (isotropic to nematic transition concentration) the semi-rigid ribbons, fibrils and fibres can align and thus transform their initially isotropic solution into a nematic liquid crystalline solution. The transition of the solution to the nematic liquid crystalline state happens at lower concentrations for more rigid polymers. For example, the nematic transition for solutions of ribbons of $P_{11}$-1 peptide occurs at $c_{I/N} \approx 13$ mM, whilst the nematic transition for solutions of the much more rigid fibrils of $P_{11}$-2 peptide occurs at $c_{I/N} \approx 0.9$ mM.

Figure 4:
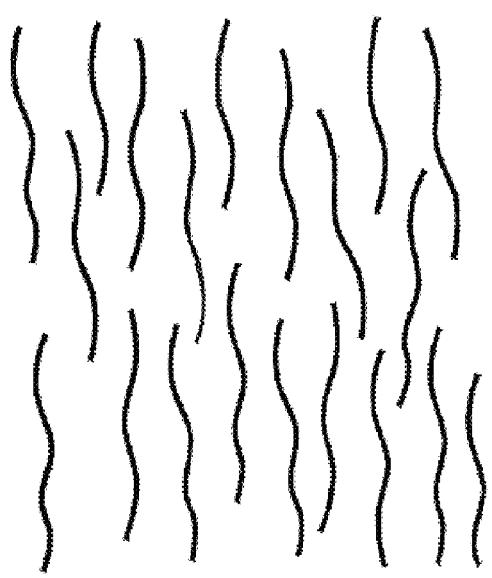
FIG. 4: Schematic representation of orientation of the semi-rigid fibrils in solution to form nematic liquid crystalline solutions. At higher peptide concentration, the fibrils entwine frequently with each other to form fibre-like junctions and cause formation of an anisotropic three-dimensional matrix and gelation of the liquid crystalline solution.
Figure 4:
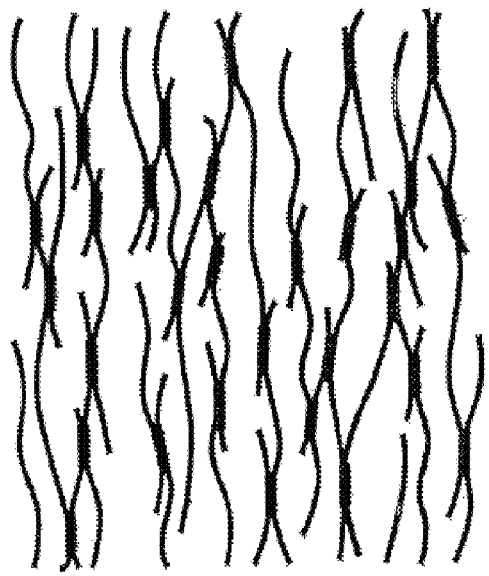

We have also shown that as the peptide concentration increases even further there is a second transition from a fluid nematic liquid crystalline solution to a self-supporting nematic gel, which is formed by the entwining of the fibrils (FIG. 4).

We have discovered that the alignment of these polymers (tapes, ribbons, fibrils and fibres) can be improved significantly by shearing or application of external magnetic field to the peptide solution. Subsequent gelation locks the aligned polymers into place and preserves their alignment for a long time (typically weeks) even after the polymer solution is removed from the magnetic field or after the end of shearing. Shearing or external magnetic field (superconducting magnet with a field strength of 7 T) have been found indeed to improve the alignment of fibrils in aqueous solutions of $P_{11}$-2 peptide, as shown by monitoring the birefringence of the solution using cross polars. The improved polymer alignment in solution has been preserved for several weeks after the end of shearing or of the application of the magnetic field.

Provided is a method of producing nematic liquid crystalline solutions and gels of homopeptide or alternating copeptide beta-sheet tapes, ribbons, fibrils or fibres with improved polymer alignment and thus improved optical properties (i.e., increased liquid crystallinity and birefringence), by shearing the peptide solutions or by subjecting them to other external forces such as electric and magnetic fields.

These peptide liquid crystalline solutions and gels can be formed in organic solvents or in water depending on the peptide design. The design of the peptide primary structure is necessary to achieve compatibility between the surface properties of the peptide polymers and the solvent. For example, self-assembling beta-sheet forming peptides with predominantly hydrophobic amino acid side-chains are required to form nematic solutions and gels in moderately polar solvents, whilst peptides which form tapes with at least one polar side are required to obtain nematic solutions and gels in water.

The fibrils and fibres are alignable and can therefore form nematic gels. Therefore, the fibrils and fibres can be spun to make, for example, high tensile strength fibres, cf. Kevlar®. Also, they can be used to make highly ordered scaffolds for tissue engineering or templates for the growth of inorganic matrices, or as matrices for the alignment of biomolecules, e.g., in NMR spectroscopy.

Until recently, formation of these polymers has been limited to relatively simple solutions (e.g., pure solvents or low ionic strength solutions). We have now discovered that it is possible to rationally design peptides which will form soluble polymers (e.g., tape, ribbons, fibrils and fibres) in more complex biologically relevant fluids, for example in cell media. These are complex mixtures used for growing and maintaining cells, because they mimic the natural environment of the cell in vivo (for the composition of typical cell media see FIG. 5). The issue of polymer solubility in these media is of practical importance. The reason is that biological fluids and cell media are characterised by relatively high ionic strength, equal to about 145 mM NaCl, which tends to cause polymers to precipitate. We have discovered that in order to produce soluble peptide polymers in these solutions, it is necessary to build an appropriate degree of repulsion between the polymers to keep them apart in solution. Stable three-dimensional gel scaffolds can be produced in cell media in this way, which precipitate from solution.

The stages of peptide design for formation of soluble beta-sheet polymers and gel scaffolds in cell media are:
1) for production of single tapes, design the peptide following the criteria in the International Patent Application No. PCT/GB96/00743. To produce stable single tapes in cell media, both sides of tapes should be covered by predominantly polar groups.
2) for production of ribbons, fibrils and fibres, one sides of the tape should be different from the other, e.g. one predominantly polar and the other predominantly apolar. The polar sides should also be able to weakly interact with each other e.g. through hydrogen-bonding sites provided for example by glutamine or asparagines side chains.
3) To ensure all these polymers are soluble in cell media, some repulsion between polymers must be created. This can be electrostatic repulsion between like charges on the polymers. Alternatively, it can be steric repulsions created by flexible solvophilic chains decorating the peptide polymers such as polyethylene glycol chains when water is the preferred solvent. These PEG segments can be attached on amino acid side-chains or on the peptide termini.

By way of illustration, we include the following example:

A large number (dozens) of systematically varied peptides (typically 7-30 residues long) have been studied for soluble polymer and gel formation in cell media. All of these peptides can self-assemble to form beta-sheet polymers in certain low-ionic strength media, but most were found to precipitate out of solution in cell media. Only peptides with a approximate net +2 or −2 charge per peptide at physiological pH=7.5, were able to form soluble polymers and gel cell media (The amount of net charge necessary per peptide to keep its polymers soluble in cell media will vary depending on the overall surface properties and solubility of the peptide tapes it forms). Amongst the peptides studied, peptides with +3 or −3 net charge per molecule exhibited only limited self-assembling capabilities in cell media at peptide concentration higher than 10 mg/ml and did not produce a gel matrix at any peptide concentration. Peptides with a +4 or −4 net charge per molecule did not self-assemble in cell media. These peptides retained a predominantly monomeric state and their solutions in cell media were fluids up to around 40 mg/ml peptide concentration.

For example, the rationally designed peptide $P_{11}$-8 in low ionic strength media at pH=7.5 does not self-assemble (peptide concentrations up to 10 mg/ml). However, when 145 mM NaCl is added in the solution or when the peptide is dissolved in cell media, it forms twisted beta-sheet fibrils, with narrow width of 4-5 nm, wide width of 12-15 nm, full pitch of 200-300 nm, and length of several micrometers.

The fibrils entwine and form a three dimensional network and turn their solution in cell media into a homogeneous self-supporting gel at peptide concentration higher than 15 mg/ml. The gel remains stable for at least several weeks at room temperature.

The gel can be broken by mechanical agitation. The time it takes to reform depends on the peptide concentration, ranging from seconds for a 35 mg/ml peptide gel, to hours for a 15 mg/ml peptide gel.

Similar behaviour was found for the rationally designed peptide $P_{11}$-8 (Table 1) in cell media. The main difference between fibrils of $P_{11}$-15 and of $P_{11}$-8 is that those formed by $P_{11}$-15 have a net −2 negative charge per peptide at pH=7.5, whilst those formed by $P_{11}$-8 have net +2 charge per peptide at pH=7.5.

Thus, peptide fibrils and gels with a variety of chemical properties can be produced by peptide design. For example, the type of charge (+ or −) of the polymer may be crucial for the polymer matrix-cell interactions. The nature of the neutral polar side-chains can also be varied to fine-tune and maximise the favourable polymer-cell interactions, and the polymer stability in vivo.

The fibrils and gels of $P_{11}$-3 and $P_{11}$-8 in cell media were found to reform after sterilisation using an autoclave. Thus autoclaving is a viable method to sterilise these peptide gels. This is significant, since sterilisation is a prerequisite for the use of these materials with cells in vitro or in vivo. Other alternative sterilisation methods that can also be used are filtration of the initially monomeric peptide solutions or gamma irradiation.

Although the peptide design procedure stated above can be used to design either tapes or higher order aggregates (i.e., ribbons, fibrils and fibres) in cell media, the more robust fibrils and fibres are potentially more useful for production of peptide scaffolds for tissue engineering. The reason is that the fibrils being much stronger structural units than e.g., tapes, can support cells in three dimensions without significant breakage for a long time. In addition, the highly packed nature of the fibrils, protects the peptides from enzymatic degradation, and can increase significantly the lifetime of the scaffold in vivo.

The peptide gels are formed with a very low peptide concentration (typically at or above 15 mg/ml), which corresponds to 0.01 volume fraction of peptide and 0.99 volume fraction of solvent in the gel, which means that the gels contain mainly solvent. Thus, encapsulated cells in these gels, have a lot of room available to grow, to communicate with each other and nutrients, oxygen, and various metabolites can diffuse almost freely in and out of the gel network.

Injection of $P_{11}$-3 and $P_{11}$-8 peptide solutions in cell media in mice has shown no effect of the presence of the peptide in the tissue surrounding the injection site as judged by histology after two and eight weeks following the peptide injection.

The opportunities that these new biomaterials provide for tissue engineering in vitro and in vivo are enormous. A large number of different cells can be encapsulated in these polymer scaffolds.

Peptides can be designed to have a self-assembling domain followed by at least one bioactive domain. Thus, polymeric gel scaffolds can be formed in cell media, decorated with specific bioactive sequences (e.g., RGD sequence) which will control the interactions of the scaffold with a particular type of cell, and also influence the growth differentiation state and function of the encapsulated cells.

The peptide polymers (especially so the more rigid fibrils and fibres) can be preferentially aligned by shearing or application of magnetic field. Thus, anisotropic polymer scaffolds can be obtained which when they are seeded with cells, they can be particularly important for the control of cell type, cell-cell interactions and shape of the growing tissue.

The cells can be encapsulated in the polymer matrix in a variety of different ways. For example:
1) disruption of gel by mechanical agitation, mixing with the cells, and encapsulation of the cells as the gel matrix reforms around them.
2) Mix the cells with an initially fluid monomeric peptide solution in cell media, followed by triggered gel formation. The trigger can be changes of the ionic strength, small pH changes, or addition of counter ions such as Ca+2.
3) Possibly the most effective way of encapsulating cells in the peptide scaffolds is using alternating copeptides. We have observed the following:

Peptides $P_{11}$-6 and $P_{11}$-7 on their own in cell medium do not self-assemble to form long beta-sheet polymers, and for this reason their solution in cell media is fluid-like rather than gel-like. Their lack of self-assembly is attributed to their high net positive and negative charges per peptide P: −6 for $P_{11}$-6 and +4 for $P_{11}$-7. When solutions of these two peptides in cell media (peptide concentration greater than 10 mg/ml) are mixed together they spontaneously transform into a self-supporting gel, owing to the formation of hetero-peptide beta-sheet polymers by these complementary interacting peptides.

Thus, it is seen that the alternating copeptide systems offer a unique way of encapsulating cells in the peptide scaffolds without the need to change the pH, ionic strength and counter ion concentration of the cell solutions. This can be done by mixing the cells with one of the initial monomeric peptide solutions, and subsequently adding the complementary peptide solution.

The heteropeptide polymers scaffolds also offer the advantage of combining different functionalities on the same polymers, and extending the chemical and periodic features of homopeptide polymers. For example one peptide component of the polymer may have a bioactive peptide bound to it, whilst its other peptide compound may have a drug molecule bound on it.

The ribbons, fibrils and/or fibres of the disclosure exhibit significant tensile strength, controlled, inter alia, by how many tapes make up the ribbons, fibrils or fibres, especially in the longitudinal direction of the fibril or fibre. Such strength has been estimated to be in the order of that of a conventional covalent bond. Furthermore, since the fibrils and/or fibres are biodegradable, because of their peptide content, they are especially advantageous in that they may be constructed into a biodegradable scaffold. Such scaffolds may comprise a weave, knit or plait of the fibrils or fibres of the disclosure.

Scaffolds can also be constructed using a combination of the peptide polymers and other commercial polymers (such as cotton and wool fibres), to obtain materials with a desirable combination of mechanical, chemical and biochemical properties, and low production cost.

Alignment of the microscopic fibrils followed by subsequent lateral association of the fibrils can result in the formation of macroscopic oriented fibre mats.

The peptide fibrils and/or fibres can be engineered to control the chemical and bioactive properties of synthetic polymer fibres. The methodology has the advantage of harnessing and combining existing expertise on manufacturing at low-cost well controlled fibrous structures with desirable mechanical properties, with the opportunity of designing their bioactivity, biocompatibility and other chemical properties. Such new materials can have exciting applications in biomedical fields such as in tissue engineering, wound healing and tissue adhesion.

Products and Applications

INDUSTRIAL APPLICATIONS

Modification of the physical and chemical properties of a surface in a controlled way, e.g., wetting properties; for example, for anti-icing applications.

Also for controlling the interaction of oil/water with clay surfaces, and the stabilising the clay itself, an important issue when, e.g., dealing with fractures in oil wells. The stability of the peptide polymers can be controlled by peptide design. Thus, by increasing the number of amino acid residues per peptide and also the number of favourable intermolecular interactions between amino acid side-chains, peptide polymers with increased stability and strength can be obtained. In addition, ribbons, fibrils and fibres can be increasingly more stable polymers compared to single tapes. Thus, the right polymers can be produced by peptide design to form gels stable in the high temperature of the oil wells. These gels can for example provide significant mechanical support at a specific site of the oil well.

Receptor or receptor binding sites can be engineered by peptide design into the ribbons, fibrils and/or fibres, providing materials for use as sensors or as biocatalysts, or as separation media in biotechnology applications.

The peptide tapes, ribbons, fibrils and fibres can be used as templates for the production of nanostructured inorganic materials with chiral pores. The dimensions, pitch and chirality of the pores can be controlled by peptide design to control the properties of the polymer aggregate. The orientation of the pores can also be controlled by alignment of the polymers in nematic states. These nanostructured materials have important applications as chiral separation media.

The fibres of the disclosure are advantageous because, inter alia, they possess similar properties to other known peptide fibres, for example, KEVLAR® which consists of long molecular chains produced from poly-paraphenylene terephthalamide. Thus the fibres of the disclosure exhibit the following features; high tensile strength at low weight, high modulus, high chemical resistance, high toughness, high cut resistance, low elongation to break, low thermal shrinkage, high dimensional stability, flame resistant and self extinguishing.

Therefore, the fibres of the disclosure can be processed into various forms, for example, continuous filament yarns, staple, floc, cord and fabric.

The processed fibres may possess the following characteristics: continuous filament yarn, high tensile strength, processable on conventional looms, twisters, cord forming, stranding and serving equipment; staple, very high cut resistance, spun on conventional cotton or worsted spinning equipment, precision cut short fibres, processable on felting and spun lace equipment; pulp-wet and dry, floc, precision cut short fibres, high surface area, miscible in blend composites, thermal resistance, excellent friction and wear resistance; cord, high tensile strength and modulus at low specific weight, retention of physical properties at high and low temperature extremes, very low heat shrinkage, very low creep, good fatigue resistance; fabric, excellent ballistic performance at low weights; and excellent resistance to cuts and protrusion combined with comfortable wear and excellent friction and wear performance against other materials.

The peptide fibrils and fibres of the disclosure may have a variety of applications, for example, in adhesives and sealants, e.g. thixotropes; in ballistics and defence, e.g., anti-mine boots, gloves—cut resistance police and military, composite helmets, and vests—bullet and fragmentation; in belts and hoses, e.g. automotive heating/cooling systems, automotive and industrial hoses, and automotive and industrial synchronous and power transmission belts; in composites, e.g., aircraft structural body parts and cabin panels, boats, and sporting goods; in fibre optic and electro-mechanical cables, e.g., communication and data transmission cables, ignition wires, and submarine, aerostat and robotic tethers; in friction products and gaskets, e.g., asbestos replacement, automotive and industrial gaskets for high pressure and high temperature environments, brake pads, and clutch linings; in protective apparel, e.g. boots, chain saw chaps, cut resistant industrial gloves, helmets—fireman and consumer (bicycle), and thermal and cut protective aprons, sleeves, etc; in tires, e.g. aircraft, automobiles, off-road, race, and trucks; and in ropes and cables, e.g., antennae guy wires, fish line, industrial and marine utility ropes, lifting slings, mooring and emergency tow lines, netting and webbing, and pull tapes.

Biomedical and Biomaterial Applications

Biocompatible Surfaces:

Bioresponsive and biocompatible surfaces to promote or to prevent adhesion, spreading and growth of endothelial cells in medical implant materials. Biocompatible surface coatings for devices such as stents, valves and other structures introduced into biological systems.

Tissue Engineering:

The peptide fibrils and/or fibres of the disclosure can be used in the construction of a biodegradable three-dimensional scaffold for use in attaching cells to produce various tissues in vivo and in vitro.

Thus according to a further feature of the disclosure we provide a three-dimensional scaffold comprising fibres or fibrils of the disclosure in cell medium. As mentioned above such scaffolds of the peptide fibrils and/or fibres are advantageous in that they can be used to support cells in the growth and/or repair of tissue. The nature of such cells may vary depending upon the nature of the tissue of interest. For example, the cells may be ligamentum cells for growing new ligaments, tenocytes for growing new tendon. Alternatively, the cells may be chondrocytes and/or other stromal cells, such as chondrocyte progenitor cells.

Therefore, according to a yet further feature of the disclosure we provide a three-dimensional scaffold comprising fibres or fibrils as hereinbefore described which scaffold is seeded with cells.

The methods of the disclosure therefore result in the efficient production of new ligament, tendon, cartilage, bone, skin, etc in vivo.

The cells may themselves be cultured in the matrix in vitro or in vivo. The cells may be introduced into the implant scaffold before, during or after implantation of the scaffold. The newly grown tissue can be used to hold the scaffold in place at the site of implantation and also may provide a source of cells for attachment to the scaffold in vivo.

The ability of the polymers to break allowing the free ends to self assemble enables, for example, scaffolds to be formed in situ and also to respond (by breaking and reforming) to the growing tissue. Also monomeric peptides may be injected at the site of choice and then chemically triggered to create, for example, a gel in situ.

Thus, according to a further feature of the disclosure we provide a method of tissue repair which comprises seeding a three-dimensional fibre matrix as hereinbefore described with appropriate cells.

For a tendon or ligament to be constructed, successfully implanted, and function, the matrices must have sufficient surface area and exposure to nutrients such that cellular growth and differentiation can occur following implantation. The organisation of the tissue may be regulated by the microstructure of the matrix. Specific pore sizes and structures may be utilised to control the pattern and extent of fibrovascular tissue in growth from the host, as well as the organisation of the implanted cells. The surface geometry and chemistry of the scaffold matrix may be regulated to control the adhesion, organisation, and function of implanted cells or host cells.

In an exemplary embodiment, the scaffold matrix is formed of peptides having a fibrous structure which has sufficient interstitial spacing to allow for free diffusion of nutrients and gases to cells attached to the matrix surface until vascularisation and engraftment of new tissue occurs. The interstitial spacing is typically in the range of 50 nm to 300 microns. As used herein, "fibrous" includes one or more fibres that is entwined with itself, multiple fibres in a woven or non-woven mesh, and sponge-like devices.

Nerve Tissue Engineering:

The fibrils and/or fibres can be used to provide paths/tracks, to control and guide the direction of growth or movement of molecules or cells. This may be useful for nerve tissue repair as well as for growth and formation of bone tissue (tissue engineering).

Bone Tissue Engineering:

Biomineralisation using the peptide ribbons, fibrils and/or fibres as a template for the nucleation and growth of inorganic materials is important in bone tissue engineering and dental applications etc. The self assembled peptide structures have been shown to be effective as templates for hydroxyapatite crystallisation, as shown in the later examples.

Self-assembling peptides may increase mineral gain via their ability to nucleate hydroxyapatite de novo and/or by decreasing mineral dissolution via stabilisation of mineral surfaces. They are therefore candidate materials for use in both caries treatment and prevention and in treatment or prevention of bone deterioration, such as that experienced in osteoporosis.

The use of peptides, e.g., self assembling peptides (SAPs), as scaffolds in in situ tissue engineering of bone is novel per se.

Thus according to a further aspect of the disclosure provided is a method of tissue engineering, e.g., tissue repair, such as of bone repair, which comprises the use of a SAP as a scaffold.

Artificial Skin:

Network structures formed from the peptide ribbons, fibrils or fibres can be used to generate artificial skin or to promote skin re-growth in vivo.

Drug Delivery:

pH and ion responsive ribbons, fibrils, fibres, gels or liquid crystals are potentially useful in drug encapsulation and release and by designing an appropriate network programmable release rates may be achieved.

Personal Care Products

Dental Applications:

Peptide ribbons, fibrils and/or fibres are of use in the protection of teeth, as carriers for delivery of active substances to promote dental repair, as templates/scaffolds for the in situ nucleation of hydroxyapatite within tooth porosities (e.g., caries lesions, dentine), as agents for the treatment and/or prevention of caries (enamel/dentine and marginal caries around restorations), as agents for the treatment and prevention of tooth sensitivity and as carriers for the delivery of active substances into teeth. In addition, the peptide structures are of application in the treatment of dentinal/tooth staining, sensitivity and other symptoms experienced in gingival recession. The use of self assembled peptide structures in caries treatment is demonstrated in the later examples.

The prior art describes use of an amphiphilic peptide as a scaffold for ordered deposition of mineral imitating crystal orientation in bone collagen [4]. This amphiphilic peptide assembles to give a structure which forms fibrils which are stabilised by covalent modification. The assembly of this peptide differs from the self assembled peptides described here in that the assembly is driven by amphiphilic forces, rather than by very specific attractions between matched groups in the separate peptide chains. The amphiphilic peptide described is not suitable for treatment in vivo as the assembly must take place at low pH (pH<4) and the covalent modification takes place under conditions hostile to living tissues. The self assembled peptide ribbons, fibrils and fibres described in this application differ in that they can be designed such that assembly is triggered at a pH and ionic strength suitable for oral application and no subsequent reaction under hostile conditions is necessary.

The prior art also describes use of casein phosphopeptides in dental application [5]. These species are not self assembling peptides as described in this application. As shown in the examples, the self assembled peptides described in this application show improved performance in mineralisation of caries like lesions of enamel under simulated oral conditions compared with the casein phosphopeptides.

In particular, we provide a method as hereinbefore described wherein the method comprises the prevention, treatment and/or alleviation of dental caries. Thus the method may comprise the mineralisation or remineralisation of a dental cavity or the suppression of leakage around existing restorations. Alternatively, the method may comprise suppression of demineralisation.

In particular, we provide a method as hereinbefore described wherein the method comprises the prevention, treatment and/or alleviation of tooth sensitivity. Thus the method may comprise the remineralisation of a dental cavity, white spot lesions or exposed dentine. Alternatively, the method may comprise suppression of demineralisation, thus preventing development of tooth sensitivity.

Although a variety of peptides may be used, one such peptide which may be mentioned is the $P_{11}$-8 peptide. A preferred group of peptides which may be mentioned are those selected from Table 1A. Table 1B, Table 1C and Table 1D.

Skin Treatments:

The controlled formation of peptide ribbons, fibrils and/or fibres can be of benefit in skincare and dermatological applications for both cosmetic and medical benefit. Benefits may include skin protection, improvement in skin feel, improvement of skin strength, increased suppleness, delivery of active or beneficial substances, moisturization, improved appearance and anti-ageing effects.

Hair Care Products:

Peptide ribbons, fibrils and/or fibres can be of benefit in hair care to improve hair condition, strength, feel, suppleness, appearance and moisturisation. Peptides which form such structures in application can be beneficial ingredients in hair shampoos, conditioners, dyes, gels, mousses and other dressings.

In another aspect of the disclosure responsive networks can be used to deliver perfumes, vitamins and/or other beneficial agents to the skin and/or hair. In particular, pH responsiveness can provide control of the delivery process.

Example 1

Synthesis, Purification and Sterilisation of Peptides

Peptides were synthesized using standard 9-fluorenyl-methoxycarbonyl (FMOC) chemistry protocols as described in Aggeli et al. (*J. Mat. Chem.*, 7:1135, 1997). Peptides were purified by reversed-phase HPLC using a water-acetonitrile gradient in the presence of 0.1% trifluoroacetic acid or ammonia as buffer A and 10% buffer A in acetonitrile as buffer B. Mass spectrometry showed the expected molecular weights. Peptides were sterilized in the dry state using γ-irradiation (2.5 MRad) with a Gammacell 1000 Elite irradiator. TEM and mass spectrometry were used to assess any damage to the peptide structure and fibril formation.

For, electron microscopy, samples were examined using a Phillips CM10 TEM at 80-100 kV accelerating voltage. Gels were diluted to a peptide concentration of 20 μM seconds before application to a glow-discharged, carbon-coated, copper grid followed by coating with uranyl acetate solution (4% w/v in water).

Example 2

Peptide $P_{11}$-8 Forms Solid-Like Gel Network of Interconnected Positively Charged Fibrils in Cell Culture Medium The rationally designed peptide $P_{11}$-8 (Tables 1A and 1C) was dissolved in 145 mM NaCl, pH~7.5 aqueous solution (the ionic strength and pH values of the solution were similar to those present in cell culture medium) or it was added directly in cell culture medium. It was found that in both solutions, $P_{11}$-8 self-assembled into twisted beta-sheet fibrils, which had typically narrow width of 4-5 nm, wide width of 12-15 nm, full pitch of 200-300 nm, and length of several micrometers.

The main difference between fibrils of $P_{11}$-3 and of $P_{11}$-8 is that those formed by $P_{11}$-3 have a net negative charge (−2)

per peptide at pH=7.5, whilst those formed by $P_{11}$-8 have net positive (+2) charge per peptide at pH=7.5.

The fibrils of $P_{11}$-8 entwined partly with each other forming a three dimensional network and turned the peptide solution in cell media into a homogeneous self-supporting gel at peptide concentration higher than 15 mg/ml. The gel remained stable for at least several weeks at room temperature.

The gel could be temporarily broken by mechanical agitation. The time it took the gel to reform depended on the peptide concentration, ranging from seconds for a 35 mg/ml peptide gel, to hours for a 15 mg/ml peptide gel.

Example 3

Contact Cytotoxicity Testing

Figure 5A:
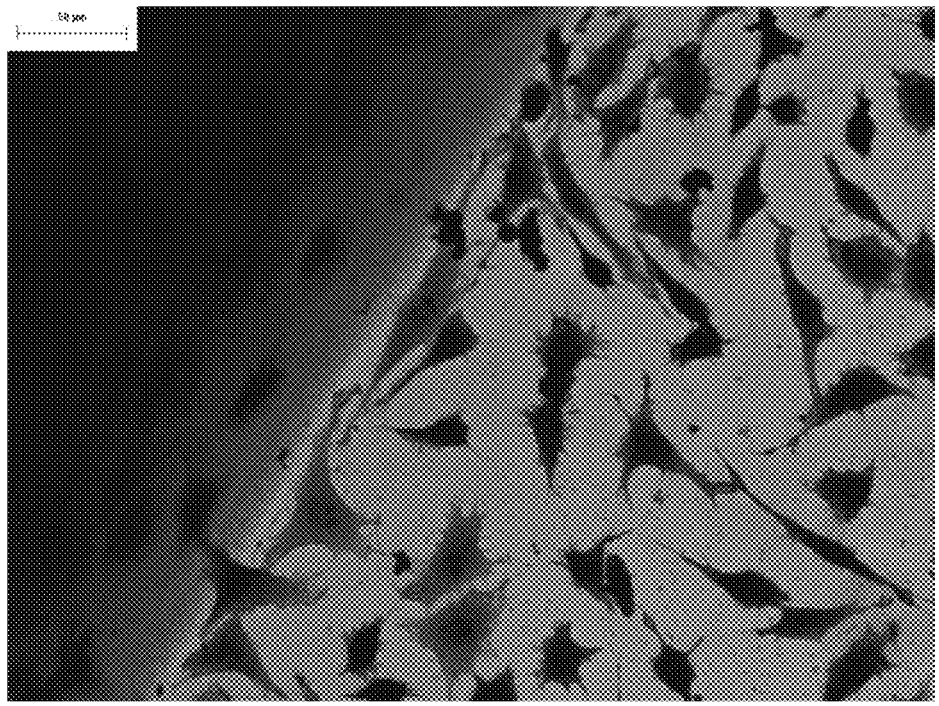
FIGS. 5A-5D: Digital optical micrograph pictures of a positive control (A) of a collagen gel and murine L929 fibroblasts, a negative control (B) and gels with peptides $P_{11}$-15 (C) and $P_{11}$-16 (D) and the murine fibroblasts growing in contact with and onto the peptide gel matrix.
Figure 5B:
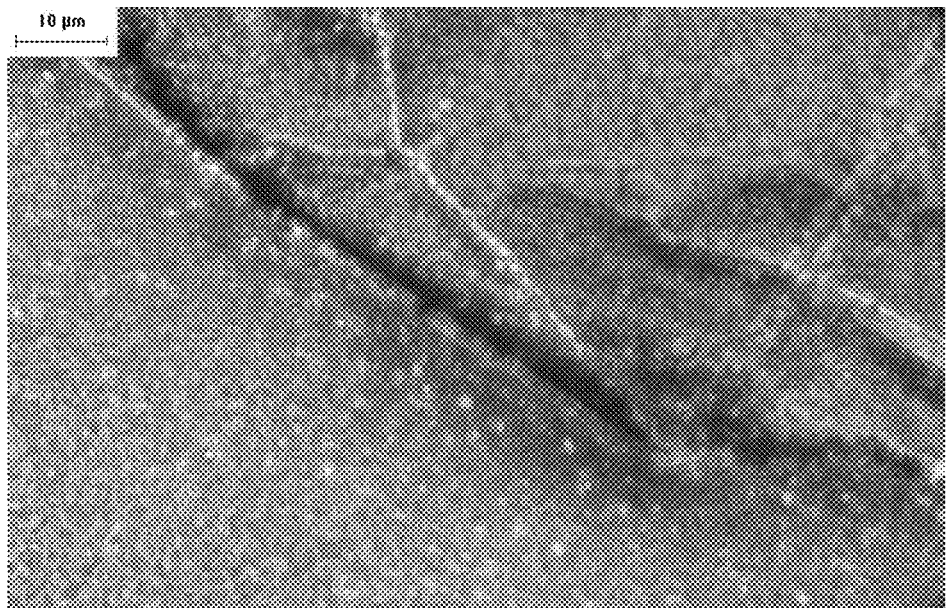
Figure 5C:
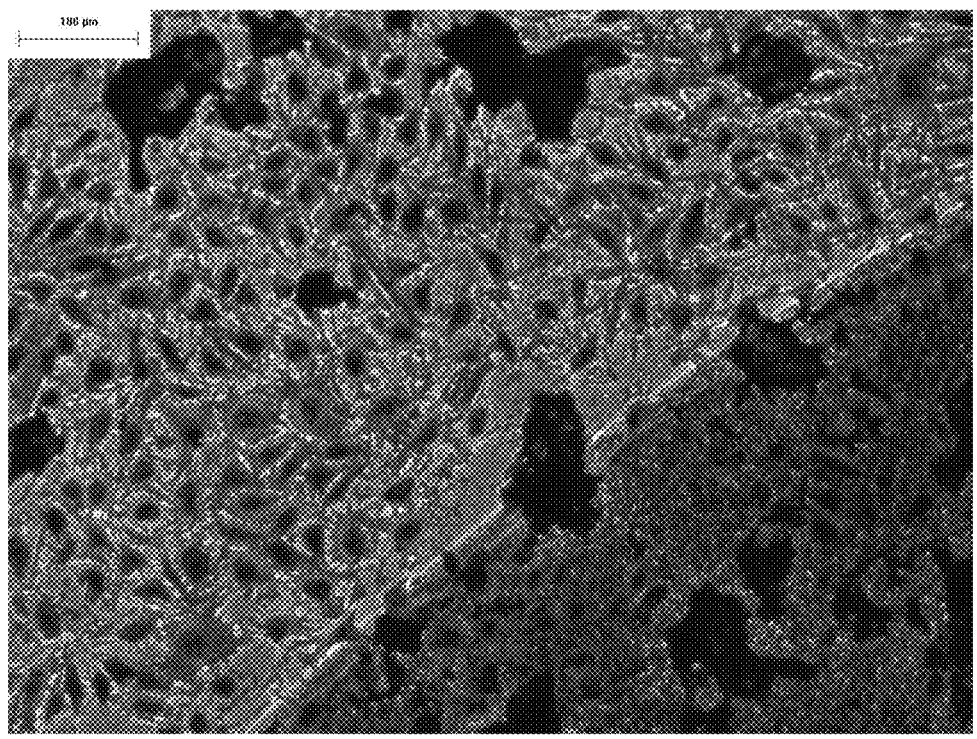
Figure 5D:
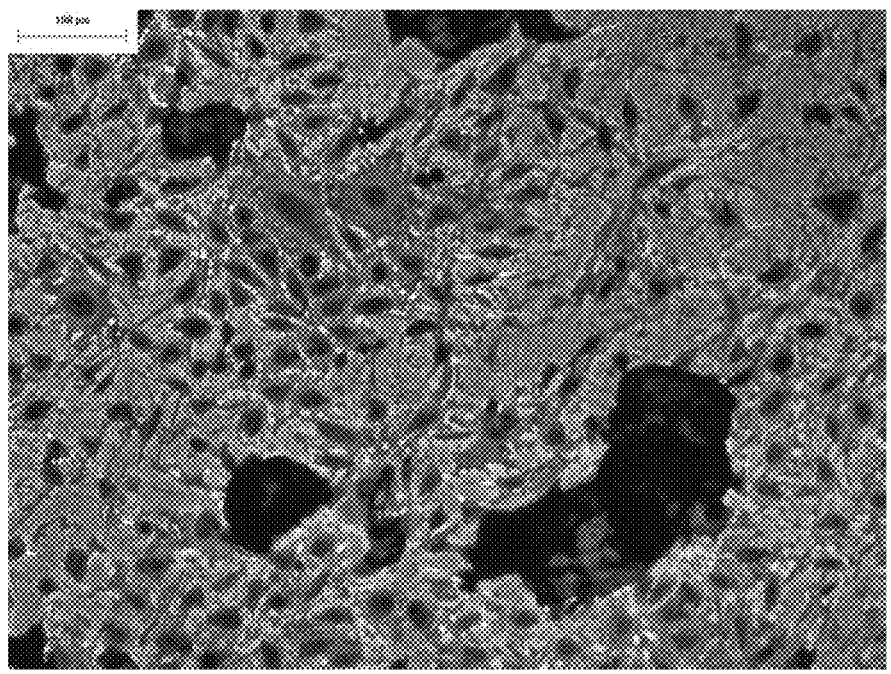
Figure 6A:
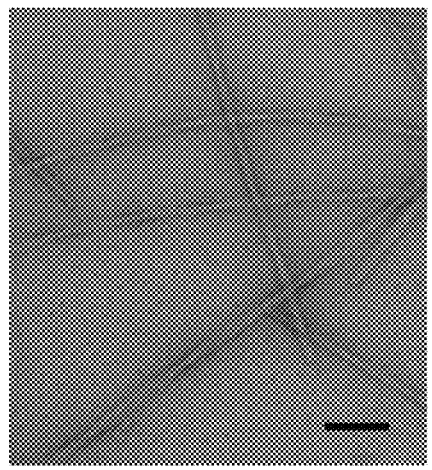
FIGS. 6A-6D: Digital TEM images of fibrils formed in a self supporting gel by peptides $P_{11}$-4 (A), $P_{11}$-9 (B), $P_{11}$-15 (C) and $P_{11}$-17 (D).
Figure 6B:
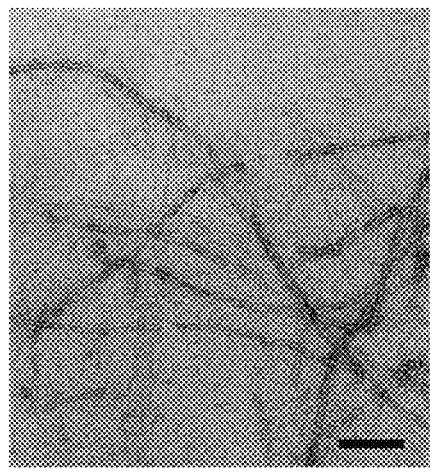
Figure 6C:
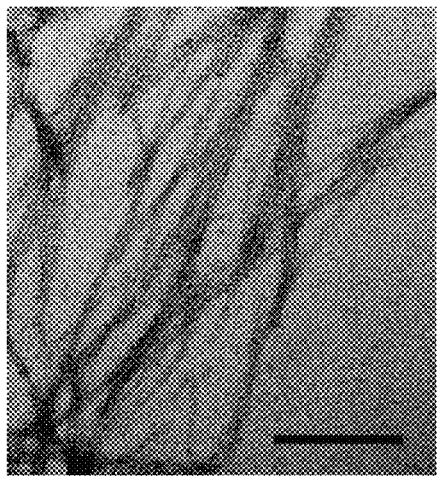
Figure 6D:
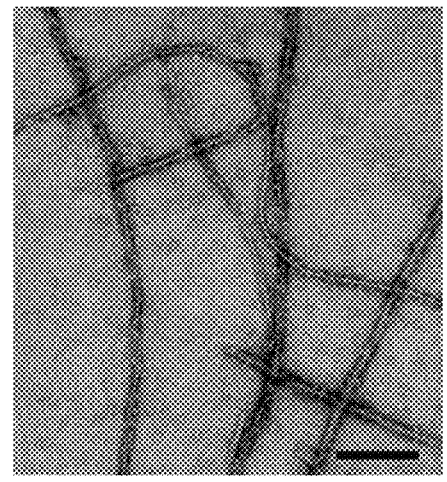

All of the self-assembling peptide gels assessed for contact cytotoxicity were found to be non-cytotoxic in these experiments. L929 murine fibroblasts growing in contact with the negative collagen control are shown in FIG. 5B and the positive control of cyanoacrylate adhesive is shown in FIG. 5A. Images showing L929 murine fibroblasts growing in contact with some of the peptides are shown in FIGS. 5C and 5D. These were typical for all the peptides and showed that the peptides tested were not cytotoxic when placed in culture with L929 fibroblast cells.

Example 4

Amphiphilic Self-Assembling Peptides Carrying a Net Negative Charge in Physiological Solution Peptides $P_{11}$-4, $P_{11}$-9, $P_{11}$-15 and $P_{11}$-17 all carry a net charge of −2 in physiological conditions. All of these peptides form self-supporting gels at peptide concentrations above 10 mg·ml$^{-1}$, and for the purposes of this study gels were prepared at a concentration of 30 mg·ml$^{-1}$.

The dimensions of the fibrils formed by these peptides are given in Table 2, and TEM images from which these measurements were obtained are shown in FIGS. 6A-6D. These dimensions are—the length of a peptide fibril (contour length, L), the length of a peptide fibril before it curves (persistence length, l), the length of a full twist of a peptide fibril (twist pitch, h) the width of a fibril at its widest point ($w_w$) and the width of the fibril at its narrowest point as it twists ($w_n$).

TABLE 2

Fibril dimensions of amphiphilic peptides carrying a net negative charge in physiological conditions.

| Peptide | L (μm)* | l (μm)* | h (nm)* | $w_n$ (nm)* | $w_w$ (nm)* |
|---|---|---|---|---|---|
| $P_{11}$-4 | 1.2-7 | 0.7-1.4 | 132-360 | 5.5-8 | 8-14 |
| $P_{11}$-9 | 1.1-5 | 0.4-1.3 | 118-236 | 3.5-7 | 7-12 |
| $P_{11}$-15 | 1.3-4 | 0.3-1.2 | 118-220 | 5-7 | 7-10 |
| $P_{11}$-17 | 1.3-4.5 | 0.3-1.7 | 150-236 | 5-10 | 10-16 |

*L is the fibril contour length, l the fibril persistence length, h the twist pitch, $w_n$ the width of the fibril at its narrowest point and $w_w$ the width of the fibril at its widest point.

Example 5

Amphiphilic Self-Assembling Peptides Carrying a Net Positive Charge in Physiological Solution The peptides $P_{11}$-8, $P_{11}$-12, $P_{11}$-16 and $P_{11}$-18 all carry a net charge of +2 in physiological conditions and all form self-supporting gels at concentrations above 10 mg·ml$^{-1}$. For the purposes of this study peptide gels were prepared at a concentration of 30 mg·ml$^{-1}$.

Figure 7A:
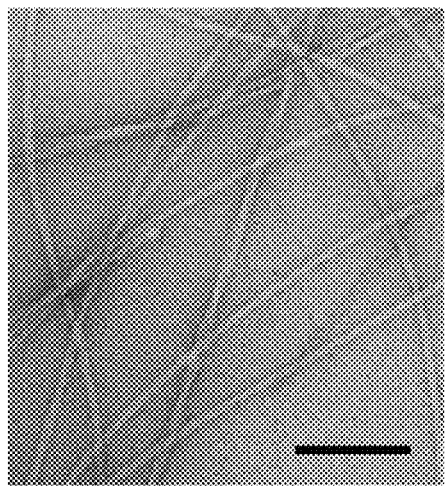
FIGS. 7A-7D Digital TEM images of fibrils formed in a self supporting gel by peptides $P_{11}$-8 (A), $P_{11}$-12 (B), $P_{11}$-16 (C) and $P_{11}$-18 (D).
Figure 7B:
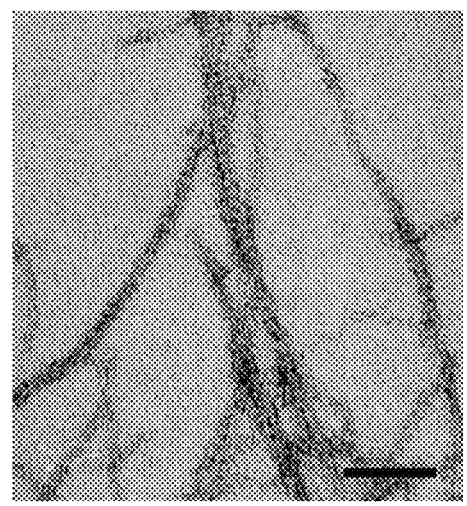
Figure 7C:
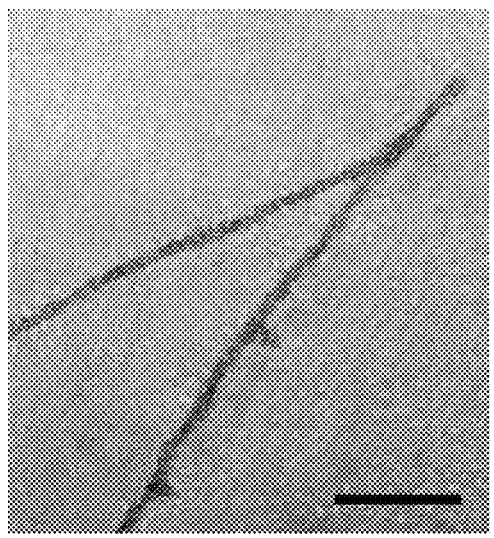
Figure 7D:
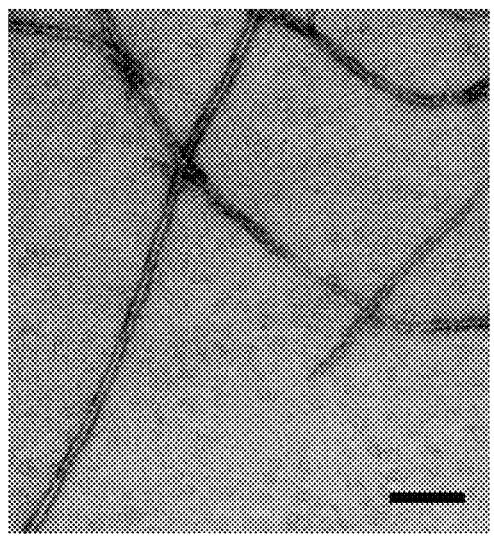

A self-supporting gel formed from peptide $P_{11}$-12 in cell culture medium is shown in FIG. 7B other TEM images of these peptides are shown in FIGS. 7A, 7C and 7D and the fibril dimensions obtained from measuring these images are shown in Table 3.

TABLE 3

Fibril dimensions of amphiphilic peptides carrying a net positive charge in physiological conditions.

| Peptide | L (μm)* | l (μm)* | h (nm)* | $w_n$ (nm)* | $w_w$ (nm)* |
|---|---|---|---|---|---|
| $P_{11}$-8 | 1.2-6.3 | 0.8-2.5 | 140-320 | 4-11 | 13-19 |
| $P_{11}$-12 | 1.3-5 | 0.4-1.2 | 139-220 | 5-7 | 11-16 |
| $P_{11}$-16 | 1.2-3.9 | 0.5-1.6 | 109-220 | 5-10 | 11-20 |
| $P_{11}$-18 | 1.4-4.2 | 0.5-1.7 | 142-236 | 7-11 | 11-21 |

*L is the fibril contour length, l the fibril persistence length, h the twist pitch, $w_n$ the width of the fibril at its narrowest point and $w_w$ the width of the fibril at its widest point.

Example 6

Polar Self-Assembling Peptides in Physiological Solution

Figure 8A:
FIGS. 8A and 8B Show digital TEM images of fibrils formed in a self supporting gel by peptide $P_{11}$-19 (A) and peptide $P_{11}$-20 (B).
Figure 8B:
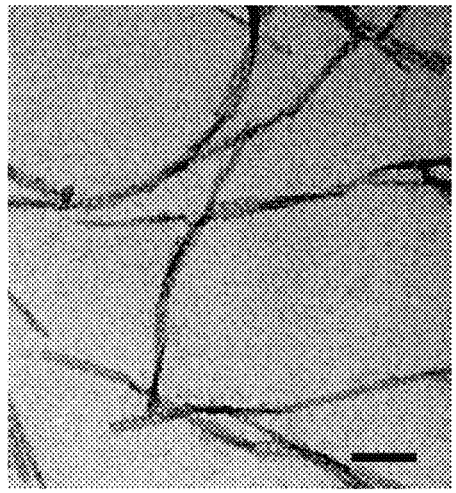

The polar self-assembling peptides are glutamine based and peptide $P_{11}$-19 carries a net charge of +2 and $P_{11}$-20 a net charge of −2. The pH responsive nature of these peptides is the same as that described for the amphiphilic positively and negatively charged peptides. $P_{11}$-20 forms a self-assembled gel at concentrations in excess of 20 mg·ml$^{-1}$, and for the purpose of this study all gels have been prepared at a concentration of 30 mg·ml$^{-1}$. $P_{11}$-19 does not self assemble at a concentration of 30 mg·ml$^{-1}$, instead forming a viscous fluid. $P_{11}$-19 does however form a self supporting gel at a peptide concentration of 60 mg·ml$^{-1}$. TEM images of peptides $P_{11}$-19 and $P_{11}$-20 are shown in FIGS. 8A and 8B, and the fibril dimensions obtained from measuring TEM images are given in Table 4. The fluorine content of peptide $P_{11}$-20 before and after freeze drying was analysed and used to calculate the amount of residual TFA in the peptide.

TABLE 4

Fibril dimensions of the polar self assembling peptides in physiological conditions.

| Peptide | L (μm)* | l (μm)* | h (nm)* | $w_n$ (nm)* | $w_w$ (nm)* |
|---|---|---|---|---|---|
| $P_{11}$-19 | 1.5-3 | 0.5-1 | 206-356 | 7-13 | 15-22 |
| $P_{11}$-20 | 0.9-2.8 | 0.4-1.5 | 202-363 | 8-15 | 14-20 |

*L is the fibril contour length, l the fibril persistence length, h the twist pitch, $w_n$ the width of the fibril at its narrowest point and $w_w$ the width of the fibril at its widest point.

All of the peptides that self-assemble to form gels at a concentration of 30 mg·ml$^{-1}$ have potential for use as scaffolds for cell culture. Altering the polar amino acids present in the peptide does not affect the ability of the peptides to self-assemble in physiological conditions. This re-enforces the hypothesis that it is the net charge of +2 or −2 that drives self-assembly in physiological conditions, and not the polar amino acid residues present. Examples 4, 5 and 6 have shown that polar peptides self-assemble forming hydrogels in physiological conditions, and not only amphiphilic peptides.

Example 7

Results of the Determination of the Cell Density in Peptide Gels by ATPLite Assay After establishing that the peptides tested were not cytotoxic when placed in culture with L929 fibroblast cells, the next stage was assessing the suitability of the collagen peptide gels for use in supporting cell proliferation.

Peptides $P_{11}$-9, $P_{11}$-12 and $P_{11}$-18 were found to be unsuccessful in supporting cell growth, especially in gels initially seeded with a low cell concentration. Peptide $P_{11}$-15 was found to be moderately successful in supporting cell growth and the gel matrices showed little sign of macroscopic degradation. Gels prepared from peptide $P_{11}$-6 which peptide had a slightly granular appearance, despite thorough mixing and appeared shrunken at the end of the experiment. Peptide $P_{11}$-7 appeared to support cell growth to some degree and peptide $P_{11}$-20 supported cell growth reasonably well but showed some signs of macroscopic degradation. Collagen gels supplemented with 0.9 mg·ml$^{-1}$ TFA supported cell growth with no obvious detrimental effect on the cells and collagen gels supplemented with 5.1 mg·ml$^{-1}$ TFA supported cell growth with no visible detrimental effect on cell growth.

It can be concluded from these studies and the initial gelation studies that negatively charged peptides form stronger gels than positively charged peptides, as the polar positively charged $P_{11}$-19 did not gel at 30 mg·ml$^{-1}$ and the amphiphilic positively charged peptides have a greater tendency to dissolve into the supernatant, as shown by the NMR studies. The positively charged peptides contain two ornithine residues with side chains ending in an —NH$_2$ functional group, whereas the negatively charged peptides contain two glutamic acid residues containing a —COOH functional group. —COOH functional groups form stronger hydrogen bonds than —NH$_2$ groups, leading to the formation of stronger aggregates. This can explain the different gelation behaviour and dissolution rates seen for the negatively and positively charged peptides.

Example 8

De Novo Precipitation of HA Inside Peptide Gels

Figure 9:
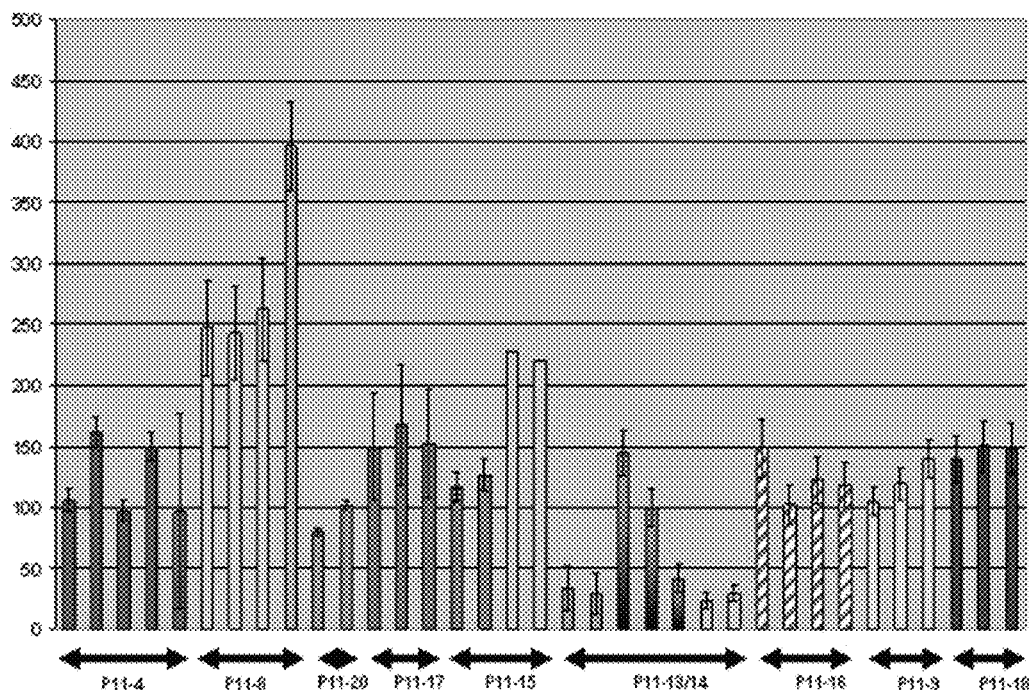
FIG. 9 Shows de novo precipitation of HA inside peptide gels for some of the peptides of the disclosure.

FIG. 9 shows the normalised phosphate values (positive control=100, negative control=0); peptides normalised against average of positive control (agar gel with polyglutamic acid present) for each run (minus average of negative controls for each run); the negative control in each case is an agar gel without any protein or peptide added in it. Differing colors/shades in each peptide set represent differing runs. A level of 100 indicates that the sample is equal to the positive control in its ability to precipitate HA de novo. A level of 0% indicates that the sample is equal to the negative control in its ability to nucleate and foster the growth of HAP.

Example 9

Effect of Increased or Decreased Charge on Gel Formation

Figure 10:
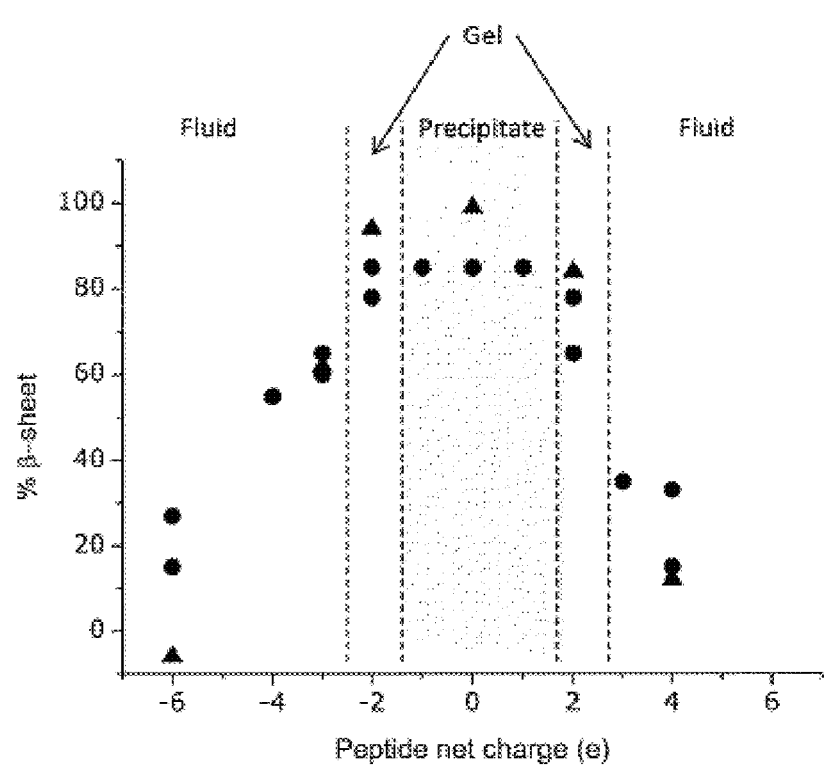
FIG. 10 is a plot showing the effect of increasing negative or positive charge on gel formation.

A summary of the experimental data that led to the conclusion that a net −2 or net +2 charge per peptide is required in order to produce stable gel scaffolds in physiological solution conditions. Table 5 shows the SAPs with increasing negative or positive net charges in physiological conditions as compared to the original $P_{11}$-2 peptide ($P_{11}$-2, SEQ ID NO: 13; $P_{11}$-21, SEQ ID NO: 14; $P_{11}$-4, SEQ ID NO: 1; $P_{11}$-22, SEQ ID NO: 15; $P_{11}$-23, SEQ ID NO: 16; $P_{11}$-13, SEQ ID NO: 5; $P_{11}$-3, SEQ ID NO: 17; $P_{11}$-8, SEQ ID NO: 2; $P_{11}$-5, SEQ ID NO: 18; $P_{11}$-14, SEQ ID NO: 6). FIG. 10 shows the beta sheet gels are formed at a net peptide charge of +2 or −2 and that a net charge of 0 or +1 or −1 the materials precipitate and above +2 or below −2 the SAPs are fluid.

TABLE 5

Amphiphilic SAPs with increasing negative or positive net charge in physiological solution conditions. The charges of primary structure compared to the original $P_{11}$-2 molecule are underlined.

| Peptide | Primary structure | Net charge at pH = 7.5 |
|---|---|---|
| $P_{11}$-2 | QQR$^+$FQWQFE$^-$QQ | 0 |
| $P_{11}$-21 | QQQFQWQFE$^-$QQ | −1 |
| $P_{11}$-4 | QQR$^+$FE$^-$WE$^-$FE$^+$QQ | −2 |
| $P_{11}$-22 | QQQFE$^-$WE$^-$FE$^+$QQ | −3 |
| $P_{11}$-23 | QQE$^-$FE$^-$WE$^-$FE$^+$QQ | −4 |
| $P_{11}$-13 | E$^-$QE$^-$FE$^-$WE$^-$FE$^+$QE$^-$ | −6 |
| $P_{11}$-3 | QQR$^+$FQWQFQQQ | +1 |
| $P_{11}$-8 | QQR$^+$FO$^+$WO$^+$FE$^+$QQ | +2 |
| $P_{11}$-5 | QQO$^+$FO$^+$WO$^+$FQQQ | +3 |
| $P_{11}$-14 | QQO$^+$FO$^+$WO$^+$FO$^+$QQ | +4 |

REFERENCES

1. Aggeli, Boden, Semenov, et al., Exploiting protein folding and misfolding to engineer nanostructured materials, *The Biochemist*, 22:10-14, 2000.
2. Nyrkova, Semenov, Aggeli, & Boden, Fibril stability in solutions of twisted beta-sheet peptides: a new kind of micellisation in chiral systems, *Eur Phys J B*, 17, 481-497, 2000.
3. Nyrkova, Semenov, Aggeli, Bell, Boden, & McLeish, Self-assembly and structure transformations in living polymers forming fibrils, *Eur Phys J B*, 17, 499-513, 2000.
4. Hartgerink, Beniash, Stupp, Self assembly and mineralisation of peptide-amphiphile nanofibers SCIENCE 294 (5547): 1684-1688, 2001.
5. Advances in enamel remineralisation: Casein phosphopeptide-amorphous calcium Phosphate. Reynolds et al. *J. Clin. Dentistry* 10: 86-88, 1999

The invention claimed is:

1. A self assembling polypeptide (SAP) that forms ribbons, fibrils or fibres in a β-sheet tape-like substructure at physiological pH and physiological salt concentrations, and wherein the polypeptide comprises $P_{11-17}$ (TTRFEWEFETT, SEQ ID NO: 9).

2. A dental product comprising the self-assembling polypeptide of claim 1.

3. A dental repair or reconstruction or preventative product comprising the self-assembling polypeptide of claim 1.

4. A tissue engineering scaffold comprising the self-assembling polypeptide of claim 1.

5. The tissue engineering scaffold according to claim 4, wherein the scaffold is seeded with cells.

6. A bone repair or reconstruction product comprising the self-assembling polypeptide of claim 1.

7. The bone repair or reconstruction product according to claim 6, wherein the product is seeded with cells.

8. A soft tissue or reconstruction product comprising the self-assembling polypeptide of claim 1.

9. A skin treatment comprising the self-assembling polypeptide of claim 1.

10. A hair care product comprising the self-assembling polypeptide of claim 1.

11. A bioresponsive and biocompatible surface comprising the self-assembling polypeptide of claim 1.

12. The self-assembling polypeptide of claim 1, comprising continuous filaments, yarns, staple, floc, cord, or fabric.

13. The self-assembling polypeptide of claim 1, further comprising a polymer.

14. The self-assembling polypeptide of claim 1, wherein the physiological pH is about 7.5.

15. The self-assembling polypeptide of claim 1, wherein the physiological salt concentration is about 145 mM NaCl.

16. A composition, comprising:
ribbons, fibrils or fibres, wherein each of the ribbons, fibrils or fibres has an antiparallel arrangement of peptides in a β-sheet tape-like substructure at physiological pH and physiological salt concentrations, wherein the composition comprises peptide $P_{11-17}$ (TTRFEWEFETT, SEQ ID NO: 9); and a physiological concentration of salt.

17. The composition of claim 16, wherein the composition comprises fibrils, and wherein the fibrils are comprised in a network of fibrils interconnected at fibre-like junctions.

18. A dental composition comprising the fibrils of claim 16.

19. A dental repair or reconstruction or preventative composition comprising the fibrils of claim 16.

20. The composition of claim 16, wherein the composition is in the form of a tissue engineering scaffold.

21. The composition according to claim 20, comprising the scaffold seeded with cells.

22. A bone repair or reconstruction composition comprising the fibrils of claim 16.

23. A soft tissue or reconstruction composition comprising the fibrils of claim 16.

24. The composition according to claim 22 that is seeded with cells.

25. A skin treatment comprising the composition of fibrils of claim 16.

26. A hair care product comprising the composition of fibrils of claim 16.

27. A part of a bioresponsive and biocompatible surface comprising the composition of fibrils of claim 16.

28. The composition of claim 16, wherein the composition comprises continuous filament yarns, staple, floc, cord, or fabric.

29. The composition of claim 16, further comprising a polymer.

30. The composition of claim 16, wherein the physiological pH is about 7.5.

31. The composition of claim 16, wherein the physiological salt concentration is about 145 mM NaCl.

32. A method of forming a tape, comprising contacting the SAP of claim 1 with an ionic aqueous medium, thereby forming a tape.

33. A method of forming a gel, comprising contacting the SAP of claim 1 with an ionic aqueous medium, thereby forming a gel.

34. A method of forming a tape, comprising contacting the composition of claim 16 with an ionic aqueous medium, thereby forming a tape.

35. A method of forming a gel, comprising contacting the composition of claim 16 with an ionic aqueous medium, thereby forming a gel.

* * * * *

SEQUENCE LISTING

<160> NUMBER OF SEQ ID NOS: 18

<210> SEQ ID NO 1
<211> LENGTH: 11
<212> TYPE: PRT
<213> ORGANISM: Artificial
<220> FEATURE:
<223> OTHER INFORMATION: self assembling peptide P11-4

<400> SEQUENCE: 1

Gln Gln Arg Phe Glu Trp Glu Phe Glu Gln Gln
1               5                   10

<210> SEQ ID NO 2
<211> LENGTH: 11
<212> TYPE: PRT
<213> ORGANISM: Artificial
<220> FEATURE:
<223> OTHER INFORMATION: self assembling peptide P11-8
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 2

Gln Gln Arg Phe Xaa Trp Xaa Phe Glu Gln Gln
1               5                   10

<210> SEQ ID NO 3
<211> LENGTH: 11
<212> TYPE: PRT
<213> ORGANISM: Artificial
<220> FEATURE:
<223> OTHER INFORMATION: self assembling peptide P11-9

<400> SEQUENCE: 3

Ser Ser Arg Phe Glu Trp Glu Phe Glu Ser Ser
1               5                   10

<210> SEQ ID NO 4
<211> LENGTH: 11
<212> TYPE: PRT
<213> ORGANISM: Artificial
<220> FEATURE:
<223> OTHER INFORMATION: self assembling peptide P11-12
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 4

Ser Ser Arg Phe Xaa Trp Xaa Phe Glu Ser Ser
1               5                   10

<210> SEQ ID NO 5
<211> LENGTH: 11
<212> TYPE: PRT
<213> ORGANISM: Artificial
<220> FEATURE:
<223> OTHER INFORMATION: self assembling peptide P11-13

<400> SEQUENCE: 5

```
Glu Gln Glu Phe Glu Trp Glu Phe Glu Gln Glu
1               5                   10

<210> SEQ ID NO 6
<211> LENGTH: 11
<212> TYPE: PRT
<213> ORGANISM: Artificial
<220> FEATURE:
<223> OTHER INFORMATION: self assembling peptide P11-14
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 6

Gln Gln Xaa Phe Xaa Trp Xaa Phe Xaa Gln Gln
1               5                   10

<210> SEQ ID NO 7
<211> LENGTH: 11
<212> TYPE: PRT
<213> ORGANISM: Artificial
<220> FEATURE:
<223> OTHER INFORMATION: self assembling peptide P11-15

<400> SEQUENCE: 7

Asn Asn Arg Phe Glu Trp Glu Phe Glu Asn Asn
1               5                   10

<210> SEQ ID NO 8
<211> LENGTH: 11
<212> TYPE: PRT
<213> ORGANISM: Artificial
<220> FEATURE:
<223> OTHER INFORMATION: self assembling peptide P11-16
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 8

Asn Asn Arg Phe Xaa Trp Xaa Phe Glu Asn Asn
1               5                   10

<210> SEQ ID NO 9
<211> LENGTH: 11
<212> TYPE: PRT
<213> ORGANISM: Artificial
<220> FEATURE:
<223> OTHER INFORMATION: self assembling peptide P11-17

<400> SEQUENCE: 9

Thr Thr Arg Phe Glu Trp Glu Phe Glu Thr Thr
1               5                   10
```

```
<210> SEQ ID NO 10
<211> LENGTH: 11
<212> TYPE: PRT
<213> ORGANISM: Artificial
<220> FEATURE:
<223> OTHER INFORMATION: self assembling peptide P11-18
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 10

Thr Thr Arg Phe Xaa Trp Xaa Phe Glu Thr Thr
1               5                   10

<210> SEQ ID NO 11
<211> LENGTH: 11
<212> TYPE: PRT
<213> ORGANISM: Artificial
<220> FEATURE:
<223> OTHER INFORMATION: self assembling peptide P11-19
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 11

Gln Gln Arg Gln Xaa Gln Xaa Gln Glu Gln Gln
1               5                   10

<210> SEQ ID NO 12
<211> LENGTH: 11
<212> TYPE: PRT
<213> ORGANISM: Artificial
<220> FEATURE:
<223> OTHER INFORMATION: P11-20

<400> SEQUENCE: 12

Gln Gln Arg Gln Glu Gln Glu Gln Glu Gln Gln
1               5                   10

<210> SEQ ID NO 13
<211> LENGTH: 11
<212> TYPE: PRT
<213> ORGANISM: Artificial
<220> FEATURE:
<223> OTHER INFORMATION: self assembling peptide P11-2

<400> SEQUENCE: 13

Gln Gln Arg Phe Gln Trp Gln Phe Glu Gln Gln
1               5                   10

<210> SEQ ID NO 14
<211> LENGTH: 11
<212> TYPE: PRT
<213> ORGANISM: Artificial
<220> FEATURE:
<223> OTHER INFORMATION: self assembling peptide P11-21

<400> SEQUENCE: 14
```

```
Gln Gln Gln Phe Gln Trp Gln Phe Glu Gln Gln
1               5                   10

<210> SEQ ID NO 15
<211> LENGTH: 11
<212> TYPE: PRT
<213> ORGANISM: Artificial
<220> FEATURE:
<223> OTHER INFORMATION: self assembling peptide P11-22

<400> SEQUENCE: 15

Gln Gln Gln Phe Glu Trp Glu Phe Glu Gln Gln
1               5                   10

<210> SEQ ID NO 16
<211> LENGTH: 11
<212> TYPE: PRT
<213> ORGANISM: Artificial
<220> FEATURE:
<223> OTHER INFORMATION: self assembling peptide P11-23

<400> SEQUENCE: 16

Gln Gln Glu Phe Glu Trp Glu Phe Glu Gln Gln
1               5                   10

<210> SEQ ID NO 17
<211> LENGTH: 11
<212> TYPE: PRT
<213> ORGANISM: Artificial
<220> FEATURE:
<223> OTHER INFORMATION: self assembling peptide P11-3

<400> SEQUENCE: 17

Gln Gln Arg Phe Gln Trp Gln Phe Gln Gln Gln
1               5                   10

<210> SEQ ID NO 18
<211> LENGTH: 11
<212> TYPE: PRT
<213> ORGANISM: Artificial
<220> FEATURE:
<223> OTHER INFORMATION: self assembling peptide P11-5
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 18

Gln Gln Xaa Phe Xaa Trp Xaa Phe Gln Gln Gln
1               5                   10
```